(12) United States Patent
Haisley et al.

(10) Patent No.: US 9,138,181 B2
(45) Date of Patent: Sep. 22, 2015

(54) MEDICAL SENSOR FOR USE WITH HEADBAND

(75) Inventors: Charles K. Haisley, Boulder, CO (US); Andy S. Lin, Boulder, CO (US); Friso Schlottau, Lyons, CO (US); Sarah Hayman, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 735 days.

(21) Appl. No.: 13/328,619

(22) Filed: Dec. 16, 2011

(65) Prior Publication Data

US 2013/0158372 A1    Jun. 20, 2013

(51) Int. Cl.
*A61B 5/1455* (2006.01)
*A61B 5/00* (2006.01)

(52) U.S. Cl.
CPC ........... *A61B 5/1455* (2013.01); *A61B 5/14552* (2013.01); *A61B 5/6803* (2013.01); *A61B 5/14553* (2013.01)

(58) Field of Classification Search
CPC ............. A61B 5/1455; A61B 5/14552; A61B 5/14551; A61B 5/6833; A61B 5/02; A61B 5/01
USPC .................................................. 600/309–344
See application file for complete search history.

(56) References Cited

U.S. PATENT DOCUMENTS

| | | | |
|---|---|---|---|
| 4,830,014 A * | 5/1989 | Goodman et al. | 600/310 |
| 5,099,842 A | 3/1992 | Mannheimer et al. | |
| 5,817,008 A | 10/1998 | Rafert et al. | |
| 5,919,133 A | 7/1999 | Taylor et al. | |
| 6,115,621 A | 9/2000 | Chin | |
| 6,144,866 A * | 11/2000 | Miesel et al. | 600/333 |
| 6,343,223 B1 | 1/2002 | Chin et al. | |
| 6,525,386 B1 | 2/2003 | Mills et al. | |
| 6,671,531 B2 | 12/2003 | Al-Ali et al. | |
| 6,748,254 B2 | 6/2004 | O'Neil et al. | |
| 7,006,855 B1 | 2/2006 | Sarussi | |

(Continued)

FOREIGN PATENT DOCUMENTS

| | | |
|---|---|---|
| EP | 1986543 | 11/2008 |
| WO | 0028888 | 5/2000 |

OTHER PUBLICATIONS

PCT Search Report for PCT Application No. PCT/US2012/068674 dated May 7, 2013, 6 pgs.

(Continued)

*Primary Examiner* — Eric Winakur
*Assistant Examiner* — Marjan Fardanesh
(74) *Attorney, Agent, or Firm* — Fletcher Yoder PC

(57) ABSTRACT

Medical sensors configured to provide enhanced patient comfort when worn over a period of time are provided. The medical sensors may include a first padding layer and a second padding layer disposed on either side of an emitter and a detector for measuring a physiological parameter of a patient. The medical sensors may also include an island padding layer secured to a patient-facing side of the second padding layer for reducing localized pressure points that may be caused by protrusions of the sensor. Additionally or alternatively, certain edges of the sensors may be rounded and/or stepped to reduce marking on the patient's tissue and to reduce strain and shear forces produced on the patient's tissue. Still further, certain embodiments provide enhanced light transmission between the emitter and detector of the sensors.

30 Claims, 13 Drawing Sheets
(1 of 13 Drawing Sheet(s) Filed in Color)

(56) References Cited

U.S. PATENT DOCUMENTS

| | | |
|---|---|---|
| 7,047,055 B2 | 5/2006 | Boas et al. |
| 7,047,056 B2 | 5/2006 | Hannula et al. |
| 7,067,893 B2 | 6/2006 | Mills et al. |
| 7,096,052 B2 | 8/2006 | Mason et al. |
| 7,190,986 B1 | 3/2007 | Hannula et al. |
| 7,190,987 B2 | 3/2007 | Lindekugel et al. |
| 7,289,837 B2 | 10/2007 | Mannheimer et al. |
| 7,359,741 B2 | 4/2008 | Sarussi |
| 7,377,794 B2 | 5/2008 | Al-Ali et al. |
| 7,440,788 B2 | 10/2008 | Jenkins et al. |
| 7,483,731 B2 | 1/2009 | Hoarau et al. |
| 7,574,245 B2 | 8/2009 | Arizaga |
| 7,657,294 B2 | 2/2010 | Eghbal et al. |
| 7,698,909 B2 | 4/2010 | Hannula et al. |
| 7,809,420 B2 | 10/2010 | Hannula et al. |
| 7,810,359 B2 | 10/2010 | Hannula et al. |
| 7,813,779 B2 | 10/2010 | Hannula et al. |
| 7,822,453 B2 | 10/2010 | Mannheimer et al. |
| 7,877,126 B2 | 1/2011 | Hannula et al. |
| 7,877,127 B2 | 1/2011 | Hannula et al. |
| 7,880,884 B2 | 2/2011 | Medina |
| 7,904,130 B2 | 3/2011 | Raridan |
| 7,979,102 B2 | 7/2011 | Hannula et al. |
| 8,071,935 B2 | 12/2011 | Besko et al. |
| 8,257,274 B2 | 9/2012 | Medina |
| 8,346,328 B2 | 1/2013 | Mannheimer et al. |
| 8,352,004 B2 | 1/2013 | Mannheimer et al. |
| 8,364,220 B2 | 1/2013 | Sandmore |
| 2004/0054291 A1 | 3/2004 | Schulz et al. |
| 2004/0122302 A1 | 6/2004 | Mason et al. |
| 2004/0267104 A1 | 12/2004 | Hannula et al. |
| 2005/0070776 A1 | 3/2005 | Mannheimer et al. |
| 2005/0197579 A1 | 9/2005 | Baker et al. |
| 2005/0222502 A1* | 10/2005 | Cooper .................. 600/323 |
| 2006/0020179 A1 | 1/2006 | Anderson et al. |
| 2006/0089547 A1 | 4/2006 | Sarussi |
| 2006/0189871 A1 | 8/2006 | Al-Ali et al. |
| 2006/0195028 A1 | 8/2006 | Hannula et al. |
| 2006/0211922 A1 | 9/2006 | Al-Ali et al. |
| 2006/0211923 A1 | 9/2006 | Al-Ali et al. |
| 2006/0211924 A1 | 9/2006 | Dalke et al. |
| 2006/0229509 A1 | 10/2006 | Al-Ali et al. |
| 2006/0241363 A1 | 10/2006 | Al-Ali et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0264726 A1 | 11/2006 | Mannheimer et al. |
| 2006/0264727 A1 | 11/2006 | Mannheimer et al. |
| 2006/0281984 A1 | 12/2006 | Mannheimer et al. |
| 2007/0038050 A1 | 2/2007 | Sarussi |
| 2007/0073122 A1 | 3/2007 | Hoarau |
| 2007/0073125 A1 | 3/2007 | Hoarau et al. |
| 2007/0078309 A1 | 4/2007 | Matlock |
| 2007/0078311 A1 | 4/2007 | Al-Ali et al. |
| 2007/0083094 A1 | 4/2007 | Colburn et al. |
| 2007/0106134 A1 | 5/2007 | O'Neil et al. |
| 2007/0142717 A1 | 6/2007 | Lowery et al. |
| 2008/0076982 A1* | 3/2008 | Ollerdessen et al. ......... 600/310 |
| 2008/0077023 A1* | 3/2008 | Campbell et al. ............. 600/502 |
| 2008/0220633 A1 | 9/2008 | Al-Ali et al. |
| 2008/0221463 A1 | 9/2008 | Baker |
| 2009/0171177 A1 | 7/2009 | Hannula et al. |
| 2010/0076276 A1 | 3/2010 | Gilland |
| 2010/0076282 A1 | 3/2010 | Sandmore |
| 2010/0081900 A1 | 4/2010 | Price |
| 2010/0081904 A1 | 4/2010 | Medina |
| 2010/0186211 A1 | 7/2010 | Macan et al. |
| 2010/0186749 A1 | 7/2010 | Macan et al. |
| 2010/0234706 A1 | 9/2010 | Gilland |
| 2010/0249551 A1 | 9/2010 | Miller |
| 2010/0249553 A1 | 9/2010 | MacLaughlin |
| 2010/0249554 A1 | 9/2010 | McKenna et al. |
| 2010/0249557 A1 | 9/2010 | Besko et al. |
| 2010/0261995 A1 | 10/2010 | McKenna et al. |
| 2010/0261996 A1 | 10/2010 | Li et al. |
| 2010/0298678 A1 | 11/2010 | Klomhaus |
| 2010/0327063 A1 | 12/2010 | Medina et al. |
| 2010/0331631 A1 | 12/2010 | MacLaughlin |
| 2011/0009723 A1 | 1/2011 | Mannheimer et al. |
| 2011/0046464 A1 | 2/2011 | Debreczeny et al. |
| 2011/0077483 A1 | 3/2011 | Boutelle |
| 2011/0112379 A1 | 5/2011 | Li et al. |
| 2011/0130638 A1 | 6/2011 | Rariden, Jr. |
| 2011/0208025 A1 | 8/2011 | Al-Ali |
| 2011/0213226 A1 | 9/2011 | Miller et al. |
| 2012/0071742 A1 | 3/2012 | Medina et al. |
| 2012/0216335 A1 | 8/2012 | McKenna et al. |
| 2012/0248985 A1 | 10/2012 | Lin et al. |
| 2012/0253148 A1 | 10/2012 | Haisley et al. |
| 2012/0253152 A1 | 10/2012 | Haisley et al. |
| 2012/0253159 A1 | 10/2012 | Medina et al. |

OTHER PUBLICATIONS

Ceelen, K.K., et al., Compression-induced damage and internal tissue strains are . . . Journal of Biomechanics (2008), doi: 10, 1016/j.jbiomech.2008.09.016.

U.S. Appl. No. 13/283,200, filed Oct. 27, 2011, Friso Schlottau.
U.S. Appl. No. 13/717,380, filed Dec. 17, 2012, Paul D. Mannheimer.
U.S. Appl. No. 61/013,850, filed Dec. 14, 2007, Carine Hourau.
U.S. Appl. No. 13/239,666, filed Sep. 22, 2011, David P. Besko.
U.S. Appl. No. 13/239,681, filed Sep. 22, 2011, David P. Besko.
U.S. Appl. No. 13/239,700, filed Sep. 22, 2011, David P. Besko.
U.S. Appl. No. 13/248,733, filed Sep. 29, 2011, Friso Schlottau.

* cited by examiner

MEDICAL SENSOR FOR USE WITH HEADBAND

BACKGROUND

The present disclosure relates generally to medical devices and, more particularly, to medical sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. These devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings may involve placement of a sensor on a patient's tissue, such as via an adhesive sensor, a clip-style sensor, or a sensor that may be fitted into or against a wearable garment, such as a hat or a headband. With regard to the latter, if the hat or headband is not closely fitted to the patient's tissue, ambient light may interfere with the sensor's light detection. Therefore, it may be desirable to ensure a tight fit of the headband to provide a suitable amount of pressure between the sensor and against the patient's tissue. However, such a tight fit may also be uncomfortable for the patient as the sensor is pressed into the patient's tissue. This can also result in an undesired amount of local exsanguination of the tissue around the sensor. Exsanguinated tissue, which is devoid of blood, may shunt the sensor light through the tissue, resulting in reduced measurement accuracy.

BRIEF DESCRIPTION OF THE DRAWINGS

The patent or application file contains at least one drawing executed in color. Copies of this patent or patent application publication with color drawings will be provided by the Office upon request and payment of the necessary fee.

Advantages of the disclosed techniques may become apparent upon reading the following detailed description and upon reference to the drawings in which.

DETAILED DESCRIPTION OF SPECIFIC EMBODIMENTS

Figure 1:
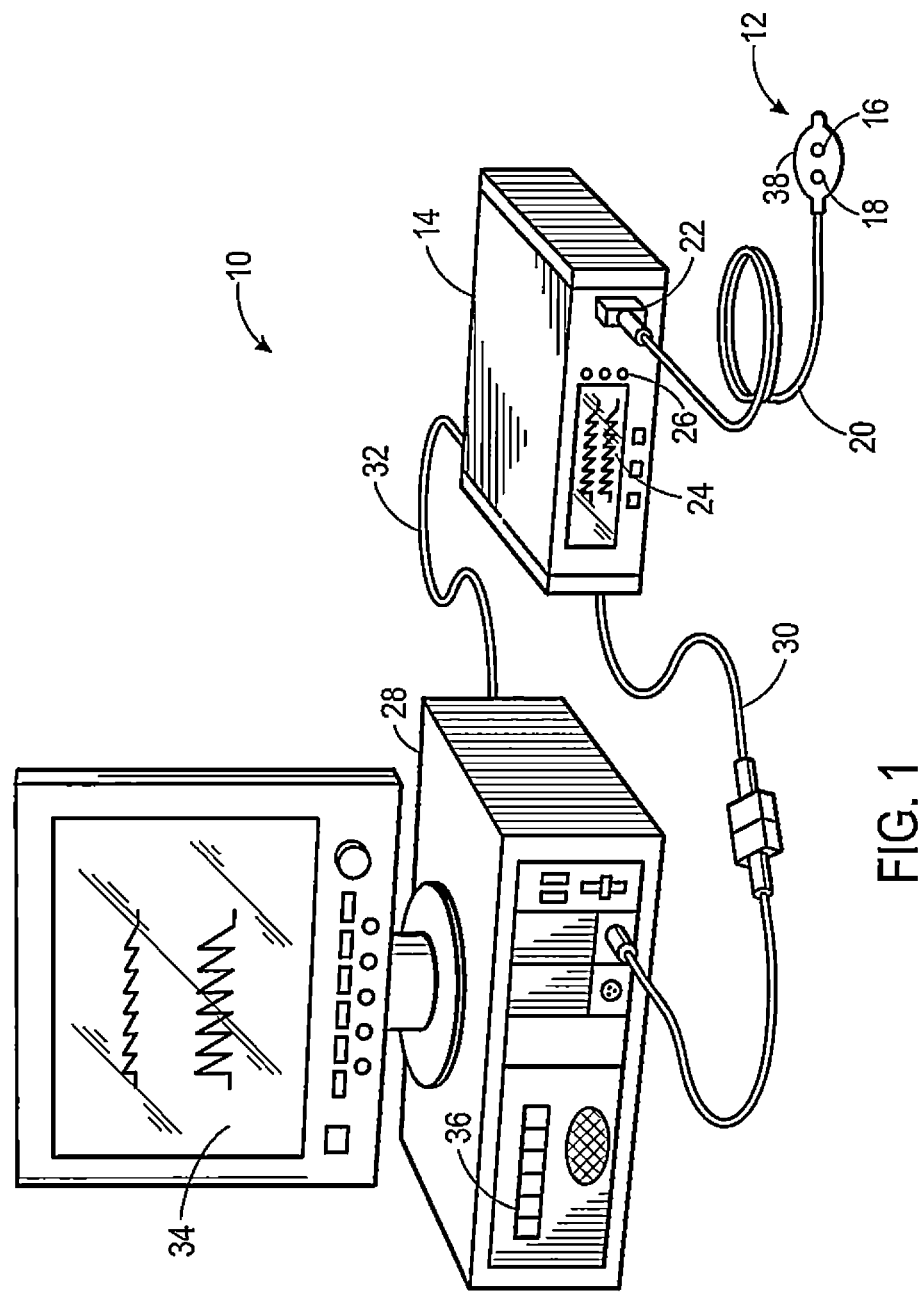
FIG. 1 a perspective view of an embodiment of a patient monitoring system configured to monitor one or more physiological parameters of a patient, and including an embodiment of a forehead oximetry sensor, in accordance with an aspect of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed above, it may be desirable to press a medical sensor tightly against a patient to increase measurement accuracy and precision. Unfortunately, the pressure created when the medical sensor is pressed against the patient's tissue can be uncomfortable for the patient. For example, lenses, edges, or similar protrusions of the medical sensor may create localized high pressure regions on the patient's tissue. These high pressure regions can lead to discomfort for the patient, can leave marks on the patient, and, in certain situations, can lead to tissue damage. Accordingly, the disclosed embodiments include medical sensors that are generally configured to enable the medical sensors, such as those used in conjunction with a headband or other wearable garment, to be snugly fit against the patient to maintain sensor performance while simultaneously maintaining patient comfort.

It should be noted that while the embodiments of the present disclosure are discussed in the context of a medical sensor for use with a headband, that sensors intended to be used with similar garments, such as hats, visors, booties, socks, wristbands, armbands, chest bands, and the like, are also presently contemplated. Thus, the embodiments disclosed herein may be implemented on any such medical sensors for use alone or in combination with wearable garments that may benefit from the techniques disclosed herein.

Embodiments of the present disclosure include medical sensors, such as pulse oximetry sensors, having features configured to reduce the occurrence of localized high pressure regions on the patient's tissue, resulting in enhanced patient comfort. By increasing the patient comfort associated with these medical sensors, their use in conjunction with headbands or similar wearable garments may be such that the garment can be applied at a tension resulting in a suitable amount of pressure for collecting accurate patient physiological data. The suitable pressure may result in increased accuracy in the measurements performed by the medical sensor.

One manner by which patient comfort may be enhanced is to mitigate the localized pressure caused by the edges of the medical sensor against the patient's tissue. For example, the edges may be stepped and/or rounded. Embodiments such as these are discussed below with respect to FIGS. 6-10. Other approaches, which may be used in combination with or in lieu of the embodiments discussed with respect to FIGS. 6-10, may include providing an extra padding material between protruding features of the sensor, such as between the optical lenses of a spectrophotometric sensor. These approaches, which may also be used alone or in any combination, are discussed in detail with respect to FIGS. 11-16. Other embodiments, which may be used with any of the embodiments discussed with respect to FIGS. 6-16 in any combination, include providing a sensor having a tapered profile, a sensor having a flat cable profile, a sensor having a flat profile at least on its patient-facing side, and a sensor having compressible optical lenses. These embodiments are discussed with respect to FIGS. 17-23.

In addition to, or in lieu of, ensuring a comfortable fit using the approaches described with respect to FIGS. 6-23, for spectrophotometric sensors, it may be desirable to increase the efficiency of light transmission through the optical lenses of the sensor. Increasing the efficiency of light transmission may enable the sensor to be used at a lower pressure than would otherwise be suitable for obtaining accurate measurements. Accordingly, the present embodiments also provide approaches for enhancing light transmission from and to the sensor by moving the emitter and/or detector closer to the patient-facing side of the medical sensor, by enhancing the internal reflectivity of the optical lenses disposed over the emitter and/or the detector, by enhancing the surface reflectivity of the kayak holding the emitter and/or the detector, or by providing enlarged openings in the emitter and/or detector wells, or any combination thereof. Such embodiments are discussed with respect to FIGS. 24-27. As noted above, any of the techniques or approaches described herein may be used in any combination.

With this in mind, FIG. 1 depicts an embodiment of a patient monitoring system 10 that may be used in conjunction with a sensor 12, such as a forehead pulse oximetry sensor, benefiting from the approaches disclosed herein. By way of example, the sensor 12 may represent an MAXFAST™, NEOMAX™, or other pulse oximetry sensor available from Nellcor Puritan Bennett, LLC. Although the depicted embodiments relate to sensors for use on a patient's forehead and/or temple, it should be understood that, in certain embodiments, the features of the sensor 12 as provided herein may be incorporated into sensors for use on other tissue locations, such as the finger, the toes, the heel, the ear, or any other appropriate measurement site. In addition, although the embodiment of the patient monitoring system 10 illustrated in FIG. 1 relates to photoplethysmography or pulse oximetry, the system 10 may be configured to obtain a variety of medical measurements with a suitable medical sensor. For example, the system 10 may additionally or alternatively be configured to perform regional oximetry, determine patient electroencephalography (e.g., a bispectral index), or any other physiological parameter.

The system 10 includes the sensor 12, which is communicatively coupled to a patient monitor 14. The sensor 12 may include one or more emitters 16 and one or more detectors 18. The emitters 16 and detectors 18 of the sensor 12 may be coupled to the monitor 14 via a cable 20. The cable 20 is configured to interface with the patient monitor 14 through a connector 22, which is adapted to couple to a sensor port of the patient monitor 14. The cable 20 may include a plurality of conductors, such as a first set for the emitter 16 and a second set for the detector 18, which are configured to carry signals (e.g., electrical signals, optical signals) between the patient monitor 14 and the sensor 12. The conductors may be surrounded by an insulting material, such that the cable 20 is a rounded cable. In other embodiments, the cable 20 may be a ribbon cable or a flexible circuit cable having a relatively flat profile, as discussed in detail below.

The patient monitor 14 includes a monitor display 24 configured to display information relating to one or more physiological parameters of the patient, information about the system 10, and/or alarm indications. The monitor 14 may include various input components 26, such as knobs, switches, keys and keypads, buttons, etc., to provide for operation and configuration of the monitor 14. The monitor 14 also includes a processor that may be used to execute code such as code for performing diagnostics on the system 10, for measuring and analyzing patient physiological parameters, and so forth.

The monitor 14 may be any suitable monitor, such as a pulse oximetry monitor available from Nellcor Puritan Bennett LLC. Furthermore, to upgrade conventional operation provided by the monitor 14 to provide additional functions, the monitor 14 may be coupled to a multi-parameter patient monitor 28 via a cable 30 connected to a sensor input port or via a cable 32 connected to a digital communication port. In addition to the monitor 14, or alternatively, the multi-parameter patient monitor 28 may be configured to calculate physiological parameters and to provide a central display 34 for the visualization of information from the monitor 14 and from other medical monitoring devices or systems. The multi-parameter monitor 28 includes a processor that may be configured to execute code. The multi-parameter monitor 28 may also include various input components 36, such as knobs, switches, keys and keypads, buttons, etc., to provide for operation and configuration of the a multi-parameter monitor 28. In addition, the monitor 14 and/or the multi-parameter monitor 28 may be connected to a network to enable the sharing of information, such as patient physiological data captured by the sensor 12, with servers or other workstations.

The sensor 12 may include a sensor body 38 housing the optical components (e.g., the emitter 16 for emitting light at certain wavelengths into a tissue of a patient and the detector 18 for detecting the light after it is reflected and/or absorbed by the blood arid/or tissue of the patient) of the sensor 12. As discussed in detail below, the sensor body 38 may be formed from any suitable material, including rigid or conformable materials, such as foam or other padding materials (e.g., a sponge or gel), fiber, fabric, paper, rubber or elastomeric compositions (including acrylic elastomers, polyimide, silicones, silicone rubber, celluloid, PMDS elastomer, polyurethane, polypropylene, polyethylene, acrylics, nitrile, PVC films, acetates, and latex).

The sensor body 38 may house a number of components, each providing certain functionality. For example, in certain embodiments, the sensor 12 may be a wireless sensor. In such embodiments, the sensor 12 may include a wireless module for establishing a wireless communication with the patient monitor 14 and/or the multi-parameter patient monitor 28 using any suitable wireless standard. By way of example, the wireless module may be capable of communicating using one or more of the ZigBee standard, WirelessHART standard, Bluetooth standard, IEEE 802.11x standards, or MiWi standard.

Figure 2:
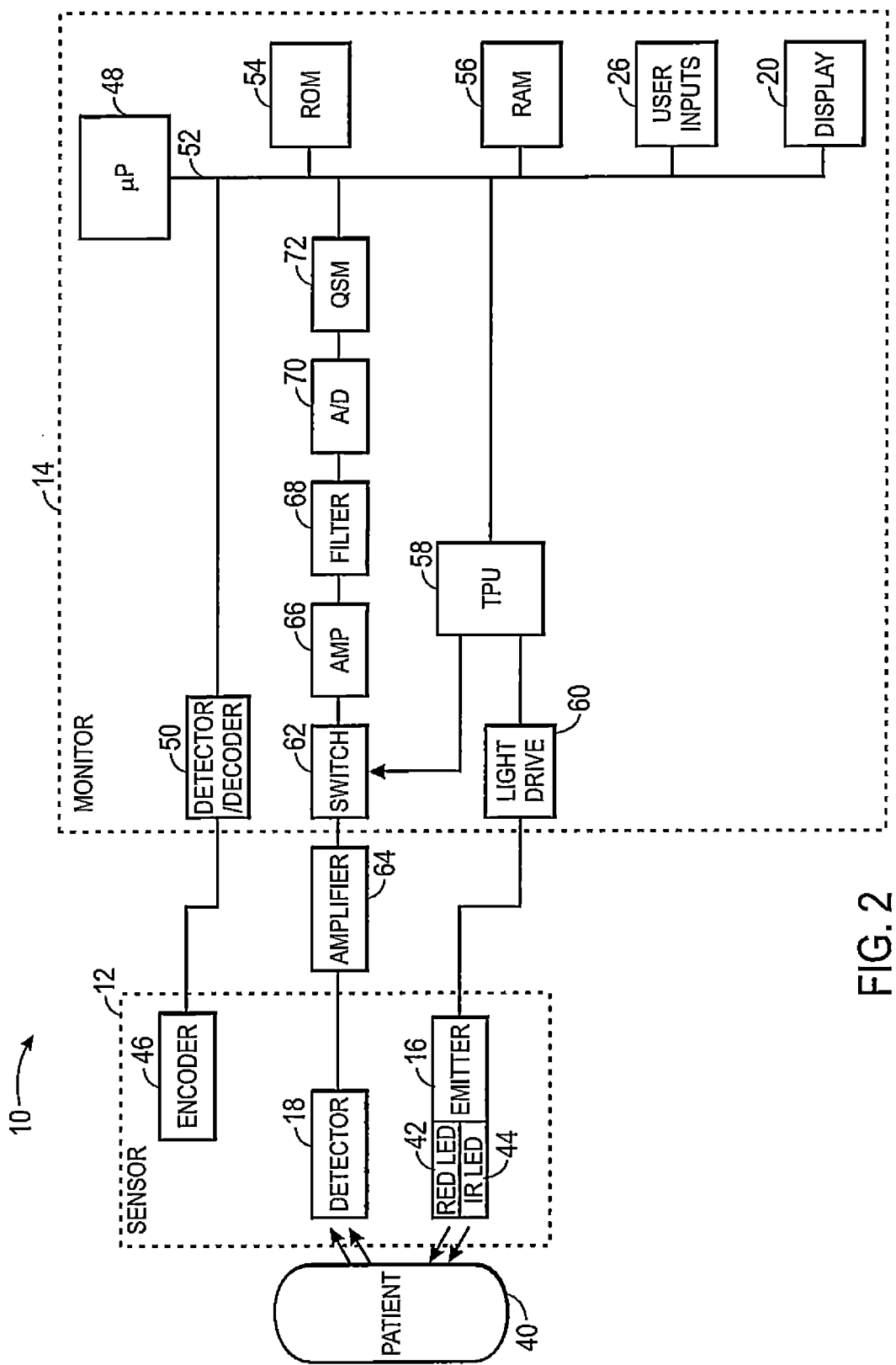
FIG. 2 is a block diagram of the components of the forehead pulse oximetry sensor and the pulse oximetry monitor of FIG. 1, in accordance with an aspect of the present disclosure.

Turning to FIG. 2, a block diagram of the system 10 is illustrated in accordance with an embodiment. The emitter 16 and the detector 18 of the sensor 12 may be arranged in a reflectance or transmission-type configuration with respect to one another. However, in embodiments in which the sensor 12 is configured for use on a patient's forehead, the emitter 16 and detector 18 may be in a reflectance configuration. The emitter 16 may include a light emitting diode, superluminescent light emitting diode, a laser diode or a vertical cavity surface emitting laser (VCSEL). The emitter 16 and detector 18 may also include optical fiber sensing elements. The emitter 16 may include a broadband or "white light" source, in which case the detector 18 could include any of a variety of elements for selecting specific wavelengths, such as reflective or refractive elements or interferometers. These kinds of emitters and/or detectors would typically be coupled to the sensor 12 via fiber optics. Alternatively, light detected from the tissue may be at a different wavelength from the light emitted into the tissue. Accordingly, in certain embodiments, the sensor 12 may be adapted to sense fluorescence, phosphorescence, Raman scattering, Rayleigh scattering and multi-photon events or photoacoustic effects (e.g., with an ultrasound receiver). In certain embodiments, the sensor 12 may be configured to perform traditional pulse oximetry measurements, regional pulse oximetry measurements, or the like. In embodiments where the sensor 12 is configured to perform regional pulse oximetry measurements, the sensor may include two or more emitters, such as two or more LEDs (e.g., four or more).

As noted above, the sensor 12 may be configured to perform traditional pulse oximetry measurements. The emitter 16 may be capable of emitting at least two wavelengths of light, e.g., red and infrared (IR) light, into the tissue of a patient 40, where the red wavelength may be between about 600 nanometers (nm) and about 700 nm, and the IR wavelength may be between about 800 nm and about 1000 nm. The emitter 16 may include a single emitting device, for example, with two LEDs 42 and 44, or the emitter 16 may include a plurality of emitting devices with, for example, multiple LED's at various locations. In some embodiments, the LEDs 42, 44 of the emitter 16 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 855-940 nm (e.g., 900 nm). Other wavelengths may include, for example, wavelengths of between approximately 500-600 nm and/or 1000-1100 nm. Regardless of the number of emitting devices, light from the emitter 16 may be used to measure, for example, oxygen saturation, water fractions, hematocrit, or other physiologic parameters of the patient 40. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In any suitable configuration of the sensor 12, the detector 18 may be an array of detector elements that may be capable of detecting light at various intensities and wavelengths. In one embodiment, light enters the detector 18 after passing through the tissue of the patient 40. In another embodiment, light emitted from the emitter 16 may be reflected by elements in the patent's tissue to enter the detector 18. The detector 18 may convert the received light at a given intensity, which may be directly related to the absorbance and/or reflectance of light in the tissue of the patient, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. After converting the received light to an electrical signal, the detector 18 may send the signal to the monitor 14, where physiological characteristics may be calculated based at least in part on the absorption and/or reflection of light by the tissue of the patient.

In certain embodiments, the sensor 12 may also include an encoder 46 that may provide signals indicative of the wavelength of one or more light sources of the emitter 16, which may allow for selection of appropriate calibration coefficients for calculating a physical parameter such as blood oxygen saturation. The encoder 46 may, for instance, be a coded resistor, EPROM or other coding devices (such as a capacitor, inductor, PROM, RFID, parallel resident currents, barcode, or a colorimetric indicator) that may provide a signal to a microprocessor 48 of the monitor 14. The signals may be related to the characteristics of the sensor 12 to enable the microprocessor 48 to determine the appropriate calibration characteristics of the sensor 12. Further, the encoder 46 may include encryption coding that prevents a disposable part of the sensor 12 from being recognized by a microprocessor 48 unable to decode the encryption. For example, a detector/decoder 50 may translate information from the encoder 46 before it can be properly handled by the processor 48. In some embodiments, the encoder 46 and/or the detector/decoder 50 may not be present.

Signals from the detector 18 and/or the encoder 46 may be transmitted to the monitor 14 via, for example, the cable 20 and the connector 22 of FIG. 1. The microprocessor described above 48 may be coupled to an internal bus 52, which is also coupled to a ROM memory 54, a RAM memory 56, the user inputs 26, and the display 24. A time processing unit (TPU) 58 may provide timing and control signals to light drive circuitry 60, which controls the timing of the emitter 16 (e.g., its activation timing), and if multiple light sources are used, the multiplexed timing for the different light sources. TPU 58 may also control the gating-in of signals from detector 18 through a switching circuit 62. These signals are sampled at the proper time, depending at least in part upon which of multiple light sources are activated, if multiple light sources are used. The received signal from the detector 18 may be passed through an amplifier 64, through the switch 62 and an additional amplifier 66, a low pass filter 68, and an analog-to-digital converter 70 for amplifying, filtering, and digitizing the electrical signals the from the sensor 12. The digital data may then be stored in a queued serial module (QSM) 72, for later downloading to the RAM 56 as the QSM 72 fills up. In an embodiment, there may be multiple parallel paths for separate amplifiers, filters, and A/D converters for multiple light wavelengths or spectra received.

In an embodiment, based at least in part upon the received signals corresponding to the light received by detector 18, the processor 48 may calculate the oxygen saturation using various algorithms. These algorithms may use coefficients, which may be empirically determined. For example, algorithms relating to the distance between an emitter 16 and various detector elements in a detector 18 may be stored in a ROM 54 and accessed and operated according to processor 48 instructions.

Figure 3:
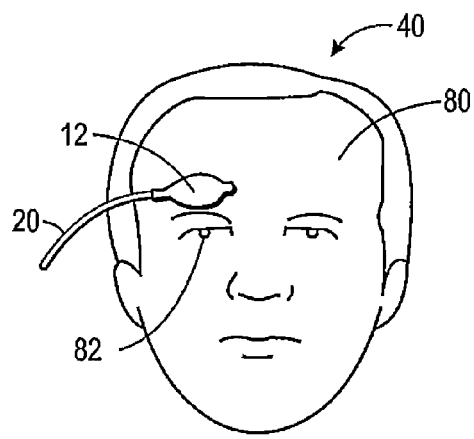
FIG. 3 is a front view of an embodiment of the forehead pulse oximetry sensor of FIGS. 1 and 2 being applied to a patient, in accordance with an aspect of the present disclosure.

As noted, the sensor 12 may be a pulse oximetry sensor configured to be placed on a patient's forehead 80, as illustrated in FIG. 3. The sensor 12 may be placed on the patient's forehead 80 in a desired location, such as above an eye 82. However, it should be noted that the sensor 12 may be placed in any region on the patient's body, such as another cerebral location or a somatic location, or a combination. For example, the sensor 12 may be placed on the patient's stomach, chest, back, or similar location. In FIG. 3, the body 38 of the sensor 12 is placed above the eye 82. For example, the body 38 of the sensor 12 may include an adhesive or other gripping surface configured to secure the sensor 12 to the patient's skin.

Figure 4:
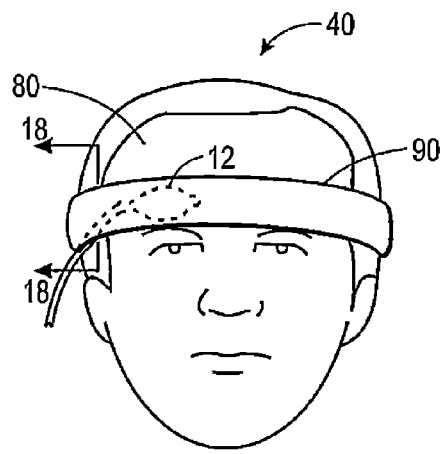
FIG. 4 is a front view of an embodiment of the forehead pulse oximetry sensor of FIG. 3 being held against a patient's forehead using a headband, in accordance with an aspect of the present disclosure.

Once the sensor 12 is positioned on the patient 40, a headband 90 may be placed around the patient's head to press the sensor 12 against the patient's forehead 80, as shown in FIG. 4. The headband 90 may have a tension setting such that when the headband 90 is suitably applied, a desired level of pressure is created between the sensor 12 and the patient's forehead 80. In some embodiments, the desired tension may be such that variations in measurements performed by the emitter 16 and the detector 18 due to venous pulsations are reduced, and the configuration of the sensor 12 may be such that exsanguination of the tissue of the forehead 80 located between the emitter 16 and the detector 18, which may cause light shunting, is prevented.

Figure 5:
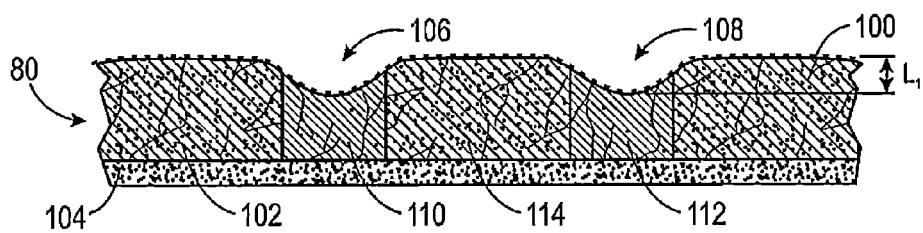
FIG. 5 is a cross-sectional view of the indentation in the patient's forehead tissue made by the pulse oximetry sensor of FIG. 3 after the application of the headband of FIG. 4, in accordance with an aspect of the present disclosure.

The headband 90, as noted above, exerts a normal force against the sensor 12 to press the sensor 12 against the patient's forehead 80, as illustrated in FIG. 5. Specifically, FIG. 5 is a cross-sectional view of a profile 100 of the sensor 12 being pressed against the patient's forehead 80. In FIG. 5, the sensor 12, as a result of the tension of the headband 90, causes portions of a tissue 102 to become compressed toward the patient's skull 104. As the sensor 12 is pressed into the tissue 102, a detector lens region 106, corresponding to a position of the detector 18, and an emitter lens region 108, corresponding to a position of the emitter 18, press into the tissue 102 by a length, $L_1$. At certain headband tensions, this may cause local reduction in blood volume, or possibly exsanguination in a first tissue region 110 and a second tissue region 112, which correspond to the area of the tissue 102 below the detector lens region 106 and the emitter lens region 108, respectively. A middle tissue region 114 remains perfuse between the exsanguinated first and second tissue regions 110, 112, and is the tissue that receives the light emitted from the emitter 16. The emitted light travels through the middle tissue region 114, and to the detector 18. In essence, a relatively higher pressure is provided in the first and second tissue regions 110, 112 by the sensor 12, while a relatively lower pressure is provided in the middle tissue region 114.

Such a configuration may be desirable to limit measurement inaccuracies caused by venous pulsations and patient movement. However, as $L_1$ increases, the level of patient discomfort and, in some situations, the possibility of damage done to the tissue 102 may increase as well. Accordingly, certain of the present embodiments are directed toward reducing $L_1$ while simultaneously limiting measurement inaccuracies caused by venous pulsations and patient movement. For example, as discussed in detail below with respect to FIGS. 11-27, the sensor 12 may include an island padding layer (FIG. 11) disposed at least between the emitter region 106 and the detector region 108, which enables the sensor 12 to mold well to the tissue 102 while providing lower pressure in the middle tissue region 114 and relatively higher pressure in the first and second tissue regions 110, 112.

Portions other than the detector and emitter regions 106, 108 of the sensor 12 may cause discomfort for the patient 40 as the sensor 12 is pressed against the patient's tissue (i.e., the forehead 80). For example, in embodiments where the sensor 12 is a pulse oximetry sensor, the sensor 12 may be placed on the patient's forehead 80 (or other region) for extended periods of time. Over time, the edges of the sensor 12 may press into the patient's tissue, which may cause discomfort and marking. Accordingly, certain of the disclosed embodiments are directed toward mitigating such discomfort by providing stepped edges of the sensor 12, which may enable the sensor 12 to readily conform to the patient's tissue as pressure is applied (e.g., by the headband 90).

Figure 6:
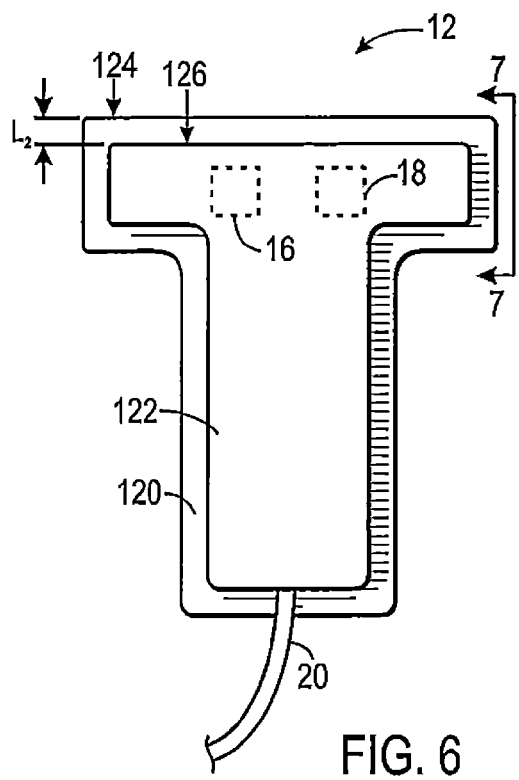
FIG. 6 is a top view of an embodiment of the forehead oximetry sensor of FIGS. 1 and 2, the sensor having a stepped edge, in accordance with an aspect of the present disclosure.
Figure 7:
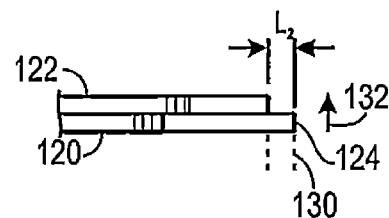
FIG. 7 is an expanded side view of an embodiment of the forehead oximetry sensor of FIG. 6, illustrating a top layer and a bottom layer as being offset from one another by a length to create the stepped edge, in accordance with an aspect of the present disclosure.
Figure 8:
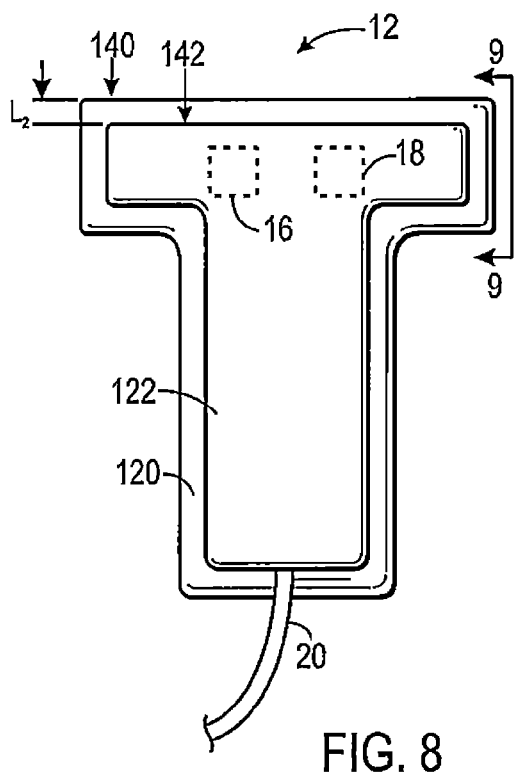
FIG. 8 is a top view of an embodiment of the forehead oximetry sensor of FIGS. 1 and 2, the sensor having a rounded and stepped edge, in accordance with an aspect of the present disclosure.

Various embodiments in which the sensor 12 has such a stepped configuration are illustrated with respect to FIGS. 6-8. Specifically, in FIG. 6, the sensor 12 includes a first padding layer 120 and a second padding layer 122. By way of example, the first padding layer 120 and the second padding layer 122 may be fabricated from the same or different padding materials, such as foam, gel, fiber, and the like. By way of example, the first and second padding layers 120, 122 may be foam layers formed from a common polyvinylchloride (PVC) foam, a polyester foam, or a polyurethane foam material, such as a PORON™ urethane foam commercially available from the Rogers Corporation of Connecticut.

The first padding layer 120 includes a first outer edge extent 124 that is greater than a second outer edge extent 126 of the second padding layer 122. That is, generally, the first padding layer 120 is greater in size than the second padding layer 122. In the illustrated embodiment, the first padding layer 120 and the second padding layer 122 are similarly shaped, and the first padding layer 120 extends beyond the second padding layer 122 evenly on all sides by a length $L_2$. However, it should be noted that the first padding layer 120 may extend beyond the second padding layer 122 by varying lengths, and, in certain embodiments, may be even with the second padding layer 122 in certain regions of the sensor 12. For example, in some embodiments, the first padding layer 120 may extend beyond the second padding layer 122 in areas of the sensor 12 that contact the patient 40 while being even with the second padding layer 122 in areas that do not contact the patient 40 or areas that experience minimal pressure when applied to the patient 40.

In use, such as when the sensor 12 is placed on the patient 40, the first padding layer 120 is configured to be closer to the patient's tissue than the second padding layer 122. Indeed, in certain embodiments, the first padding layer 120 may be secured to an adhesive layer, or may include an adhesive layer, that is configured to secure the sensor 12 to the patient 40. As illustrated in FIG. 7, which is a partial side view of the sensor 12 of FIG. 6 along line 7-7, the first padding layer 120 includes a deformable region 130. The deformable region 130 is generally defined by the length $L_2$ separating the outer extents of the first and second padding layers 120, 122, and is configured to deform in a first direction 132 generally away from the patient 40 as the sensor 12 is applied to the patient 40. This deformation of the first padding layer 120 may result in a reduction in the localized pressure or tissue-shear regions typically caused by the edges of a sensor placed against a patient. In other words, the edge 124 of the first padding layer 120 may deform away from the patient 40 to prevent the edge 124 from pressing into the patient's tissue.

Figure 9:
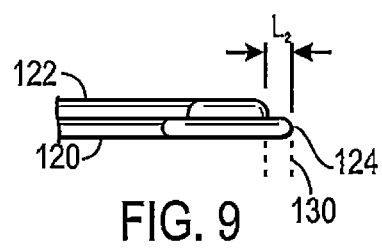
FIG. 9 is an expanded side view of an embodiment of the forehead oximetry sensor of FIG. 8, illustrating a rounded top layer and a rounded bottom layer as being offset from one another by a length to create the stepped edge, in accordance with an aspect of the present disclosure.
Figure 10:
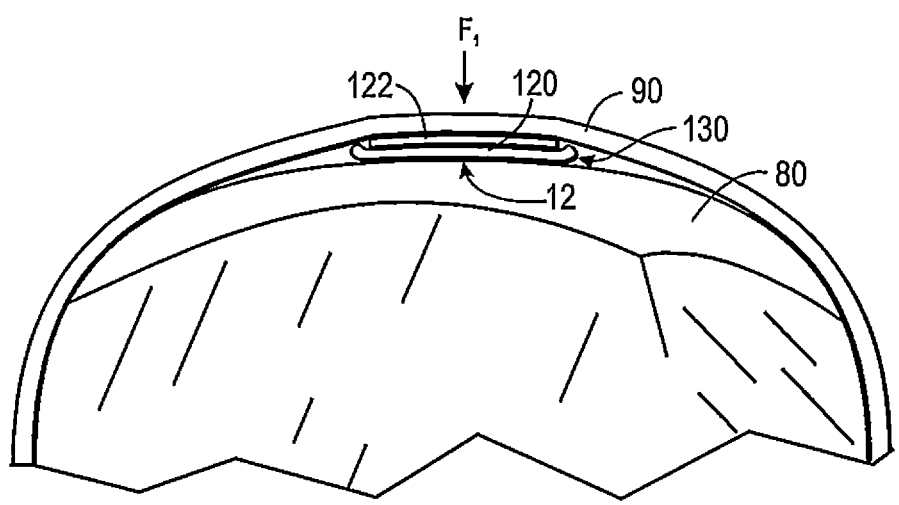
FIG. 10 is a top view of an embodiment of the sensor of FIGS. 6 or 8 being held against a patient's forehead using a headband, the sensor having a stepped edge so as to reduce localized pressure against the patient's forehead tissue, in accordance with an aspect of the present disclosure.

As an alternative, or in addition to, providing stepped edges to mitigate patient discomfort, the present disclosure also provides embodiments in which the sensor 12 includes rounded or filleted edges. FIG. 8 depicts an embodiment of the sensor 12 in which the first and second padding layers 120, 122 have respective rounded edges 140, 142. As in FIGS. 6 and 7, the first padding layer 120 extends beyond the second padding layer 122 by the length $L_2$ to create a stepped edge configuration for the sensor 12. Therefore, as shown in FIG. 9, which is a partial side view of the sensor 12 of FIG. 8 along line 9-9, the first padding layer 120 includes the deformable region 130, which is capable of deforming away from the patient 40 to prevent localized pressure region formation. It should be noted that while the embodiment of the sensor 12 illustrated in FIGS. 8 and 9 includes the rounded edges 140, 142 for both the first and second padding layers 120, 122, in other embodiments, only the first padding layer 120 may have a rounded edge. Therefore, in certain embodiments, the first padding layer 120 may have the rounded edge 140 in addition to, or in lieu of, rounded edges for any one or a combination of other layers of the sensor 12. As defined herein, a rounded edge is intended to denote a general curvature of a surface connecting two faces of a layer. Thus, the rounded edges 140, 142 for the first and second padding layers 120, 122, respectively, are defined by a curved surface connecting a patient-facing surface of each layer with an outward-facing surface of the respective layer.

As noted above, portions of the sensor 12 having a stepped edge configuration may conform to the patient's tissue while in use. For example, in FIG. 10, the sensor 12 is depicted as secured (e.g., adhesively or non-adhesively) to the patient 40, and a normal force, $F_1$, is being applied to the sensor 12 by the headband 90. As illustrated, the deformation region 130 of the first padding layer 120 curls back toward the second padding layer 122 due, at least in part, to the application of the normal force $F_1$ by the headband 90 and the resistance of the patient's tissue to the normal force $F_1$. The patient 40 may experience enhanced comfort as a result of such a configuration, as the edge of the sensor 12 (i.e., the rounded edge 140 of the first padding layer 120) may not press into the patient's forehead 80 by an appreciable extent.

The disclosed approaches for reducing localized pressure against the patient's forehead 80, such as the use of stepped and/or rounded edges (i.e., edges having a curvature), may be used together or separately, or in any combination with other techniques presently disclosed for increasing patient comfort. For example, stepped and/or rounded edges may be used in combination with any of the embodiments depicted in FIGS. 11-18 and 20-22, which each illustrate an embodiment of the sensor 12 having an island padding layer 150. As noted above with respect to FIG. 5, the island padding layer 150 may enable the sensor 12 to apply adequate pressure so as to accurately measure a physiological parameter while maintaining the pressure at a comfortable level for the patient 40.

Figure 11:
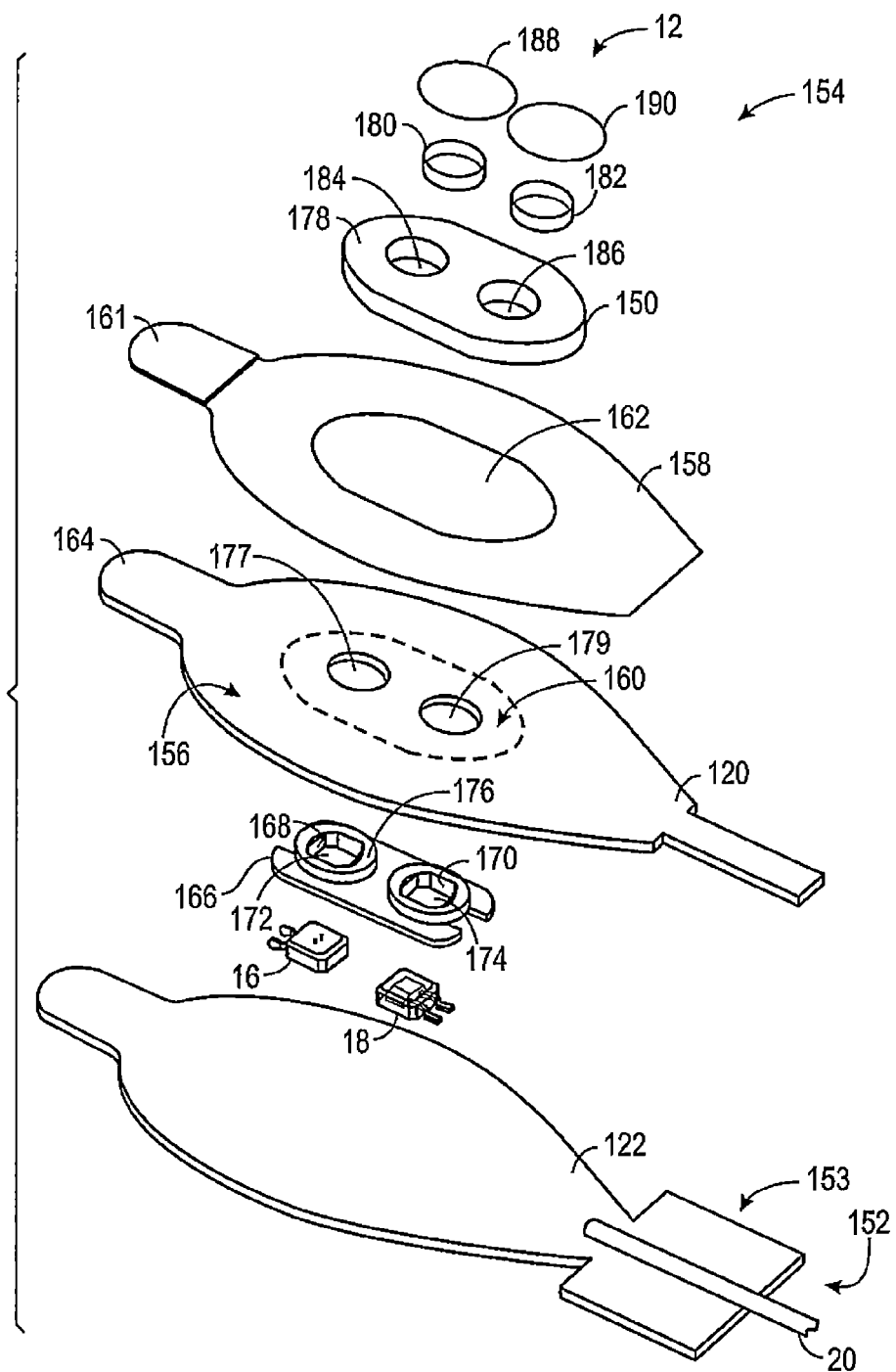
FIG. 11 is a perspective exploded view of an embodiment of the sensor of FIGS. 1 and 2 and illustrating components of the sensor that are configured to reduce the pressure of the sensor against a patient's tissue, in accordance with an aspect of the present disclosure.

One such embodiment of the sensor 12 is depicted in FIG. 11, which is an exploded perspective view of the sensor 12. Specifically, the illustrated embodiment of the sensor 12 includes the island padding layer 150 in addition to the first and second padding layers 120, 122. Generally, the padding layers 120, 122, 150 are configured to provide support for the sensing components (e.g., the emitter 16 and the detector 18) of the sensor 12 and/or to provide padding for patient comfort. As illustrated, the second padding layer 122 is configured to act as an outermost layer disposed on a first side 152 of the sensor 12 generally away from the patient 40. Essentially, the second padding layer 122 is configured to face away from the patient 40 and, in embodiments where the sensor 12 is used in conjunction with the headband 90, is configured to be placed in abutment with the headband 90. Conversely, the island padding layer 150 is disposed toward a second side 154 of the sensor 12 and is configured to be placed in direct contact with the patient 40. The embodiment of the second padding layer 122 depicted in FIG. 11 also includes a cable wrap region 153, which is configured to wrap around the cable 20 to maintain the position of the cable 20 within the sensor 12. However, in certain embodiments, it may be desirable to not include the cable wrap region 153 to reduce the bulkiness of the sensor 12 in the region where the cable 20 interfaces with the sensor 12.

As illustrated, an outer section 156 of the first padding layer 120 couples to a patient-contacting adhesive layer 158 for securing the sensor 12 to the patient, while an inner section 160 of the first padding layer 120 couples (e.g., directly via a coated adhesive or indirectly by a supported transfer tape) to the island padding layer 150. Thus, the patient-contacting adhesive layer 158 may include a central opening 162 corresponding to the position of the island padding layer 150 to enable the island padding layer 150 to attach to the first padding layer 120. It should be noted that in embodiments where the sensor 12 is a stacked adhesive medical sensor, multiple patient-contacting adhesive layers may be provided. Accordingly, a tab 161 may be provided on each patient-contacting adhesive layer 158 for easy removal, such as when the sensor 12 is removed from the patient 40 for re-positioning.

Further, while the illustrated embodiment depicts the sensor 12 as including the patient-contacting adhesive layer 158, in other embodiments, the sensor 12 may not include the patient-contacting adhesive layer 158. For example, the tension of the headband 90 may provide a sufficient securing force such that the sensor 12 remains secured to the patient's forehead 80 without the use of an adhesive. Additionally, in certain of these embodiments where the headband 90 is used, a gripping material with a relatively high coefficient of friction may be disposed on a patient-facing surface 164 of the first padding layer 120 to reduce movement of the sensor 12 while the patient 40 is monitored.

In addition to the padding layers discussed above, the sensor 12 of FIG. 11 also includes a semi-rigid optical mount 166 disposed between the first and second padding layers 120, 122 for surrounding and holding the emitter 16 and the detector 18. The semi-rigid optical mount 166 is configured to hold the emitter 16 and the detector 18 in a fixed manner while allowing a certain minimal amount of flexing and twisting to occur. The semi-rigid optical mount 166 also may be referred to as a "kayak" because of the way it holds the emitter 16 and the detector 18 in place. It should be noted that the semi-rigid optical mount 166 may prevent torque from causing orientation changes between the emitter 16 and the detector 18, which could interfere with the accuracy of measurements obtained by the detector 18 due to motion-induced artifacts and changes in calibration. Moreover, the optical mount 166 may serve as a shunt barrier between the emitter 16 and detector 18, and may be made of a material having a relatively high degree of optical absorbance, such as a black polypropylene material. However, in certain embodiments, first and second wells 168, 170 of an emitter opening 172 and a detector opening 174, respectively, may be white or another optically reflective color so as to enhance light transmission between the emitter 16 and the detector 18 along the desired optical path (i.e., through the patient 40). By way of example, the first and second wells 168, 170 may be painted or otherwise coated with a reflective material, such as a white paint. In certain embodiments, when the sensor 12 is assembled, a top surface 176 of the semi-rigid optical mount 166 may be substantially flush with a patient-facing surface 164 of the first padding layer 120. Thus, the semi-rigid optical mount 166 may position the emitter 16 and the detector 18 within first and second emitter opening 177, 179, respectively, of the first padding layer 120.

The sensor 12 is also illustrated as including an emitter lens 180 and a detector lens 182 which, when the sensor 12 is assembled, are positioned within at least a second emitter and detector opening 184, 186 of the island padding layer 150 and are each disposed on the surface 176 of the semi-rigid optical mount 166. The emitter lens 180 and the detector lens 182 may be pre-fabricated lenses (e.g., gel lenses, plastic lenses), or may be molded lenses that are formed within the emitter and detector openings 184, 186. Thus, the emitter lens 180 and the detector lens 182 may each be recessed within the island padding layer 150, substantially flush with the patient-facing surface 178 of the island padding layer 150, or protrude beyond the patient-facing surface 178 of the island padding layer 150. The emitter and detector lenses 180, 182 may be formed from any suitable lens material that is substantially transparent with respect to the wavelengths of light used for the measurements performed by the sensor 12. As discussed in further detail below with respect to FIGS. 20 and 21, the emitter lens 180 and the detector lens 182 may be pre-formed lenses formed from a compressible material. By way of example, the emitter lens 180 and the detector lens 182 may have a hardness on the Shore OO durometer scale of less than approximately 60, less than approximately 40, or less than approximately 20. In one embodiment, the emitter lens 180 and the detector lens 182 may include or be entirely formed from a silicone gel. It should be noted, however, that in certain embodiments, the hardness of the lenses 180, 182, the padding layers 120, 122, 150, or any combination thereof, may be measured or quantified based on other durometer hardness scales, such as the Shore A durometer scale.

The hardness of the emitter lens 180 and the detector lens 182 may be selected to be greater than a hardness of the island foam layer 150. For example, the emitter lens 180 and the detector lens 182 may have a hardness on the Shore OO durometer scale that is between approximately 1 and 500% higher, such as between approximately 10 and 400%, 50 and 350%, or 100 and 300% higher than a hardness on the Shore OO durometer scale of the island foam layer 150. In this way, as the sensor 12 is pressed against the patient 40 (e.g., the forehead 80), the emitter lens 180 and the detector lens 182 create a minor indentation into the tissue 102 (FIG. 5) while the island foam layer 150 prevents $L_1$ (FIG. 5) from becoming sufficiently large so as to cause discomfort for the patient 40.

First and second circular tapes 188, 190 may cover the emitter lens 180 and the detector lens 182 to prevent the emitter and detector lenses 180, 182 from sticking to the patient 40 and to keep the emitter and detector lenses 180, 182 relatively free of debris. The first and second circular tapes 188, 190 may include any single-sided supported adhesive approved for use in conjunction with medical devices. The first and second circular tapes 188, 190 may be transparent with respect to wavelengths of light used by the sensor to measure the one or more physiological parameters of the patient 40. Thus, it may be desirable to provide the first and second circular tapes 188, 190 as separate pieces with a sufficient separation distance therebetween to prevent light shunting through the tapes 188, 190. It should be noted that while the tapes 188, 190 are presented in the context of having circular cross-sectional geometries, other cross-sectional shapes are also presently contemplated. For example, tapes having cross-sectional polygonal (e.g., triangular, square, rectangular, hexagonal) shapes and/or rounded (e.g., oval, elliptical, semi-circular) shapes are also presently contemplated.

Further, in other embodiments, the sensor 12 may not include the circular tapes 188, 190. For example, the lenses 180, 182 may be selected from materials that are not readily removed from the sensor 12, or may include features that reduce the possibility of their removal from the sensor 12. Indeed, as discussed with respect to FIG. 29, in certain embodiments the emitter and/or detector lenses 180, 182 may be flanged to facilitate their retention within the sensor 12 without the use of the circular tapes 188, 190. In still further embodiments, an adhesive may be disposed within the emitter and detector openings 184, 186 to retain the emitter and detector lenses 180, 182 within the sensor 12.

Figure 12:
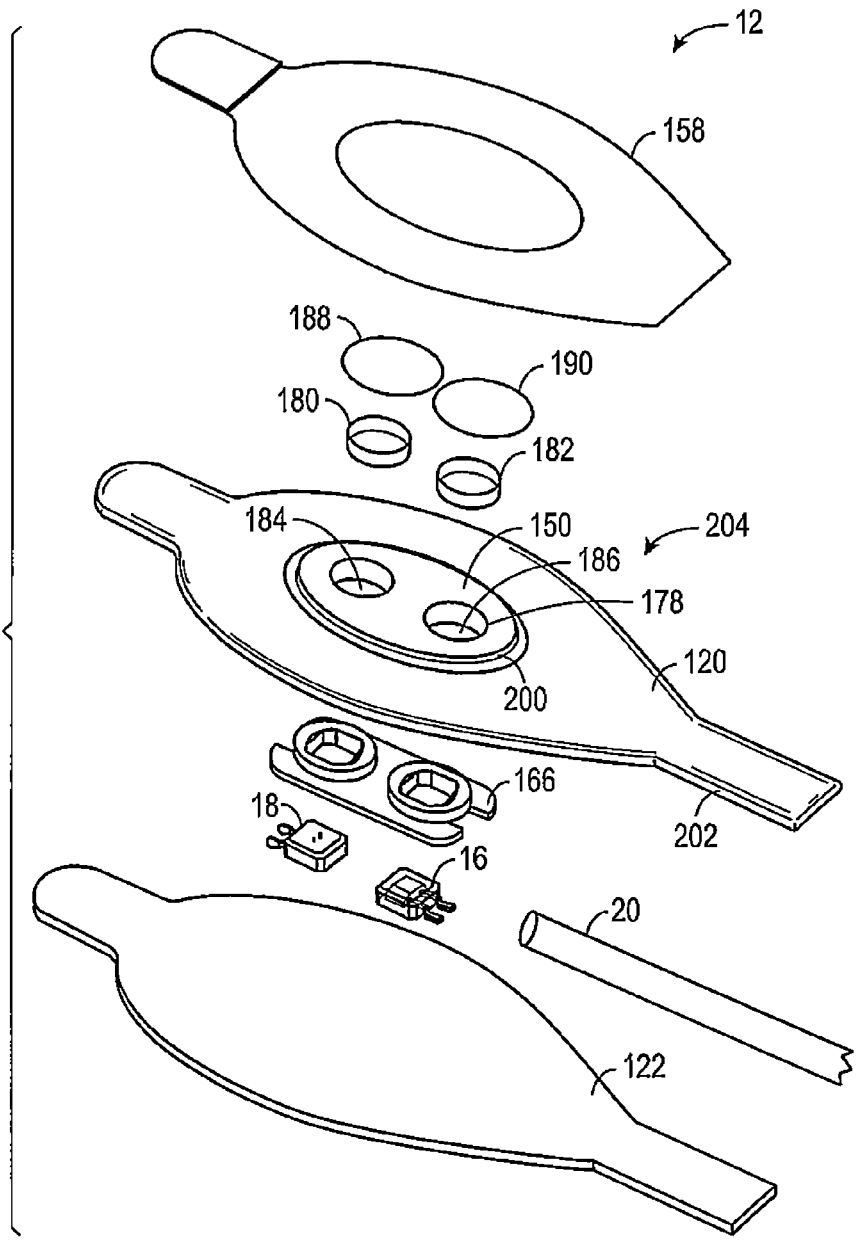
FIG. 12 is a perspective exploded view of an embodiment of the sensor of FIGS. 1 and 2 and illustrating components of the sensor that are configured to reduce the pressure of the sensor against a patient's tissue, in accordance with an aspect of the present disclosure

While the embodiment of the sensor 12 depicted in FIG. 11 includes non-rounded edges (e.g., straight edges), in certain embodiments it may be desirable to provide rounded edges (i.e., curved or rounded edges) to prevent patient discomfort. For example, localized pressure regions, or regions of relatively high tissue shear, may result from pressing the edges of the sensor 12 into the patient 40, such as when the sensor 12 is used in conjunction with the headband 90. Accordingly, FIG. 12 illustrates an embodiment of the sensor 12 in which the island padding layer 150 and the first padding layer 120 have respective rounded edges 200, 202. Additionally, the island padding layer 150 and the first padding layer 120 are depicted as being formed as a single molded piece 204. Forming the island padding layer 150 and the first padding layer 120 as the single molded piece 204 may shorten an assembly process of the sensor 12 by removing at least one assembly step (e.g., attaching the island padding layer 150 to the first padding layer 120), which may reduce the costs and increase the efficiency associated with the construction of sensors in accordance with present embodiments.

Figure 13:
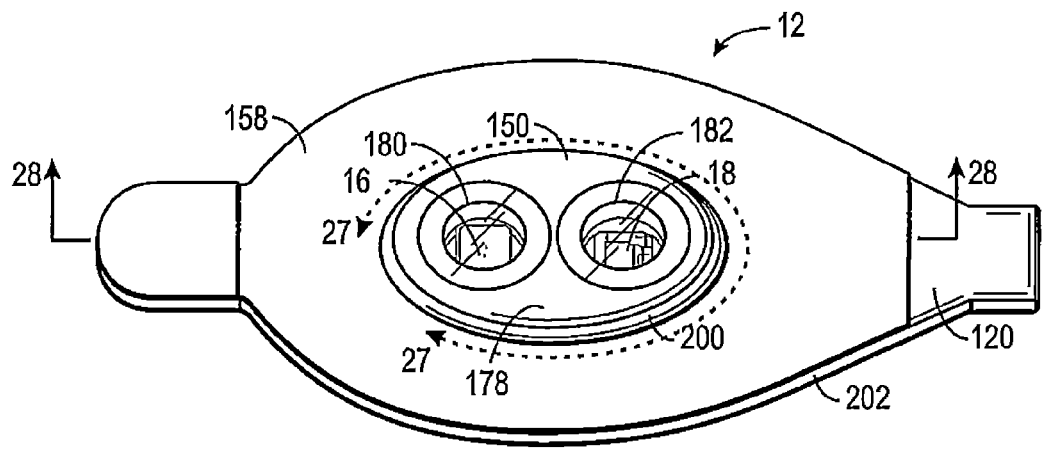
FIG. 13 is a perspective view of the sensor of FIG. 12 in its assembled form, in accordance with an aspect of the present disclosure.

As noted above, the emitter lens 180 and the detector lens 182 may each be recessed within the island padding layer 150, substantially flush with the patient-facing surface 178 of the island padding layer 150, or protrude beyond the patient-facing surface 178 of the island padding layer 150. Such embodiments are illustrated with respect to FIGS. 13-16. Specifically, the assembled form of the embodiment of the sensor 12 of FIG. 12 is illustrated in FIG. 13. As illustrated, the emitter 16 and the detector 18 are recessed within the island padding layer 150, while the emitter lens 180 and the detector lens 182 each stand slightly proud of the patient-facing surface 178 of the island padding layer 150. The island padding layer 150 and the first padding layer 120 are also depicted as including the rounded edges 200, 202, which are configured to reduce the potential for patient discomfort as the sensor 12 is worn for an extended period of time. That is, the rounded edges 200, 202 are configured to prevent sharp edges of the sensor 12 from pressing into the patient 40.

Figure 14:
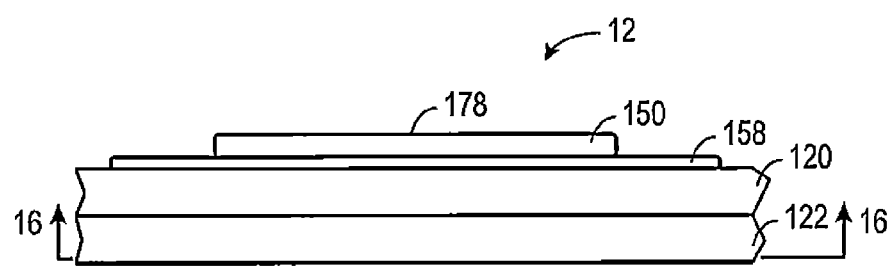
FIG. 14 is a side view of an embodiment of the sensor of FIGS. 11 or 12 in its assembled form and having lenses that are substantially flush with a padding of the sensor, in accordance with an aspect of the present disclosure.

Alternatively, as illustrated in the side cutaway view of the sensor 12 in FIG. 14, the emitter lens 180 and the detector lens 182 may each be substantially flush with the patient-facing surface 178 of the island padding layer 150, or positioned below the patient-facing surface 178 of the island padding layer 150. Such a configuration may be desirable in embodiments where the emitter lens 180 and the detector lens 182 may have a hardness that is substantially greater than a hardness of the island padding layer 150. For instance, as the sensor 12 is pressed into the patient tissue 102 (FIG. 5) (e.g., by the headband 90), the island padding layer 150 may compress to a point where the emitter lens 180 and the detector lens 182 may protrude beyond the patient-facing surface 178. The degree to which the emitter lens 180 and the detector lens 182 may protrude may be tailored to provide a desired magnitude of $L_1$ (FIG. 5) for producing a suitable level of pressure to ensure accurate measurements while also maintaining patient comfort.

Figure 15:
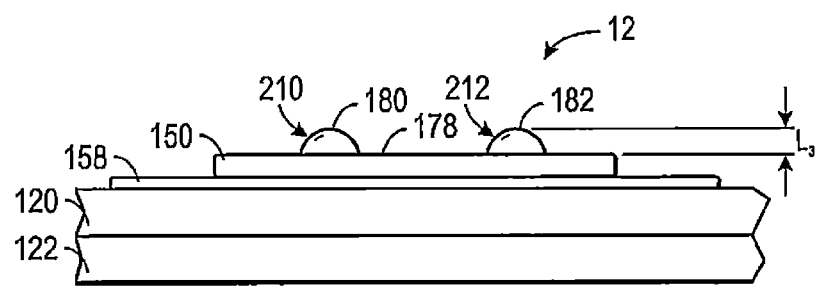
FIG. 15 is a side view of an embodiment of the sensor of FIGS. 11 or 12 in its assembled form and having lenses that protrude beyond a padding of the sensor, in accordance with an aspect of the present disclosure.

As noted above, the emitter and detector lenses 180, 182 may be formed within the emitter and detector openings 184, 186 of the island padding layer 150. Such an embodiment is depicted in FIG. 15, which illustrates the emitter and detector lenses 180, 182 as being formed during assembly of the sensor 12 from a curable mixture, such as a siloxane mixture, an epoxy mixture, a PVC mixture, or the like. Again, the emitter and detector lenses 180, 182 may be formed from materials that are substantially transparent with respect to the wavelengths of light used by the emitter 16 and the detector 18 for measuring the one or more physiological parameters of the patient 40. Further, the emitter and detector lenses 180, 182 may each include respective patient-facing surfaces 210, 212, which may be substantially flat as depicted in FIGS. 11-13, or may be rounded as depicted in FIG. 15. In embodiments where the respective patient-facing surfaces 210, 212 of the emitter and detector lenses 180, 182 protrude beyond the patient-facing surface 178 of the island padding layer 150, a length or distance $L_3$ between the outermost portion of the respective patient-facing surfaces 210, 212 and the patient-facing surface 178 of the island padding layer 150 may correspond to $L_1$ (FIG. 5). For example, in embodiments where the island padding layer 150 is not substantially compressed when the sensor 12 is placed on the patient 40, $L_1$ may be substantially equal to $L_3$. However, in embodiments where the island padding layer 150 is compressed as the sensor 12 is positioned, $L_1$ may be greater than $L_3$ before placement, and substantially equal to $L_3$ after placement (i.e., as the island padding layer 150 compresses, $L_3$ may increase).

Figure 16:
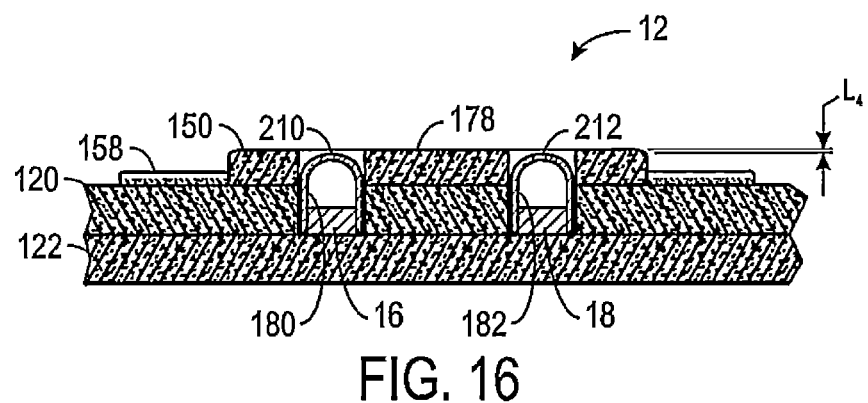
FIG. 16 is a cross-sectional view taken within line 16-16 of FIG. 14 and illustrating an embodiment of the sensor of FIGS. 11 or 12 in its assembled form and having lenses that are positioned underneath a padding of the sensor, in accordance with an aspect of the present disclosure.

In embodiments where the respective patient-facing surfaces 210, 212 are positioned below the patient-facing surface 178 of the island padding layer 150, as illustrated in the cross-sectional side view of FIG. 16 taken within line 16-16 of FIG. 14, a length or distance $L_4$ may separate the outermost portion of the respective patient-facing surfaces 210, 212 and the patient-facing surface 178 of the island padding layer 150. Accordingly, as the sensor 12 is placed on the patient 40, the island padding layer 150 may be compressed to an extent such that patient-facing surfaces 210, 212 extend beyond the patient-facing surface 178 of the island padding layer 150 by the desired $L_1$ (FIG. 5).

Figure 17:
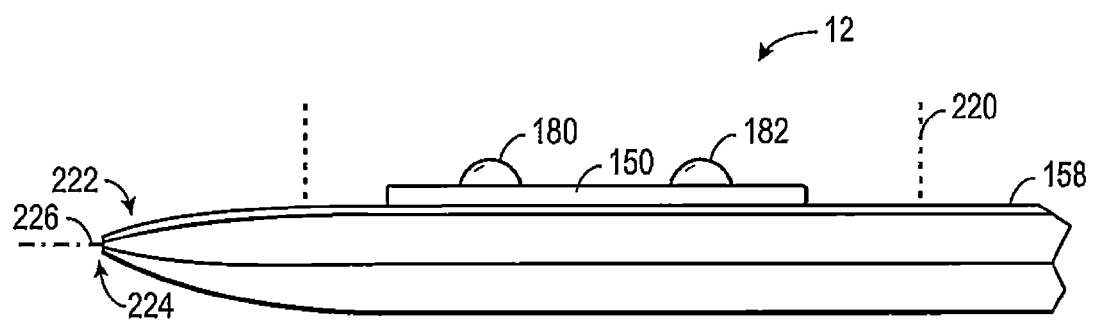
FIG. 17 is a side view of an embodiment of the sensor of FIGS. 11 or 12 in its assembled form and having tapered padding layers, in accordance with an aspect of the present disclosure.

In addition to or in lieu of any of the embodiments described above, which may be used alone or in any combination, it may be desirable to provide flattened portions of the sensor 12, such as portions of the padding layers 120, 122, 150, the cable 20, or any combination thereof, to reduce or eliminate edges that may create areas of localized pressure. Such embodiments are described with respect to FIGS. 17-19. Specifically, FIG. 17 illustrates an embodiment of the sensor 12 having a tapered configuration. In the illustrated embodiment, the first and second padding layers 120, 122 have a relatively flat profile in an area 220 of the sensor 12 proximate the island padding layer 150, and have a tapered region 222 toward an outer edge 224 of the sensor 12. The first and second padding layers 120, 122 each taper toward a central axis 226 of the sensor that is positioned generally along the interface between the first and second padding layers 120, 122. Further, it should be noted that while only one portion of the sensor 12 (i.e., the edge 224) is depicted as including the tapered region 222, the tapered region 222 may extend around the entire perimeter of the sensor 12, or along a plurality of perimeter regions of the sensor 12. The tapered configuration may be desirable to decrease the pressure created between the edges 224 of the sensor 12 and the patient's tissue 102 (FIG. 5). For example, in one embodiment, the outer edges 224 may not contact the patient 40 even after the headband 90 has been applied, due to the tapered configuration. In other embodiments, the pressure of the sensor 12 may be greater in the central area 220 than the edges 224 having the tapered region 222, which may decrease or eliminate the possibility of the edges 224 pressing into the patient's tissue 102.

Figure 18:
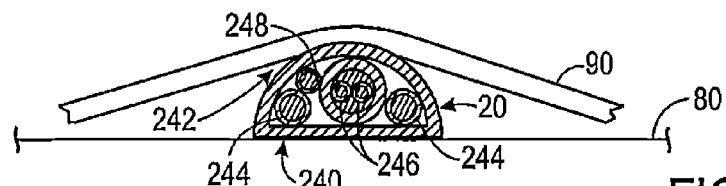
FIG. 18 is a cross-sectional view of the sensor cable taken within line 18-18 of FIG. 4, the sensor cable having a flat side of the facing the patient's tissue, in accordance with an aspect of the present disclosure.

In addition to, or in lieu of, providing flattened or tapered padding layers as discussed above, it may be desirable for the cable 20 to have at least a partially flattened profile so as to prevent relatively high levels of pressure of the cable 20 against the patient 40 as the sensor 12 is held against the patient 40 by the headband 90. For example, it will be appreciated upon reviewing the illustration in FIG. 4 that at least a portion of the cable 20 may be disposed between the headband 90 and the patient's forehead 80. Accordingly, in situations where the cable is a conventional cable having a rounded profile, the cable 20 may uncomfortably press against the patient's forehead 80 due to a relatively high localized pressure. FIG. 18, which is a cross-sectional view of the cable 20 taken within line 18-18 of FIG. 4, illustrates an embodiment of the cable 20 having a flat profile.

As illustrated in FIG. 18, the cable 20 is being pressed against the patient's forehead 80 by the headband 90 such that a flat portion 240 of the cable 20 is in abutment with the patient's forehead 80. A rounded portion 242 of the cable 20 is in direct abutment with the headband 90 to cause the cable 20 to be pressed against the patient's forehead 80. The cable 20 includes a first set of conductors 244 configured to transmit signals between the emitter 16 and the monitor 14 and a second set of conductors 246, which are configured to transmit signals between the detector 18 and the monitor 14 (FIG. 1). The cable 20 also includes a drain wire 248, which is configured to ground a Faraday shield (not shown) of the detector 18. Further, it should be noted that while the illustrated embodiment depicts the cable 20 as having the flat portion 240 and the rounded portion 242, in other embodiments, the cable 20 may be a ribbon cable, or any similar cable having only a flat profile. For example, the cable 20 may include a relatively flat dielectric substrate on which the conductors 244, 246, 248 are printed using a metal ink. Indeed, any cable capable of reducing pressure experienced by the patient 40 as the cable 20 is held against the patient 40 by the headband 80 is presently contemplated and may be used in conjunction with any of the embodiments described herein.

Figure 19:
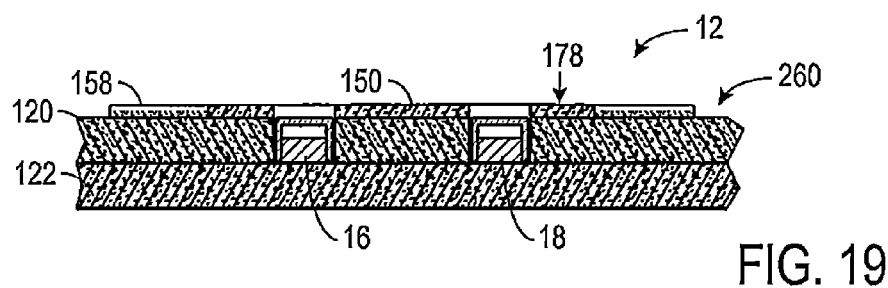
FIG. 19 is a cross-sectional view of an embodiment of the sensor of FIGS. 11 or 12 and illustrated as having an adhesive layer of the sensor substantially flush with a padding layer of the sensor, in accordance with an aspect of the present disclosure.

In addition to, or in lieu of, providing the cable 20 having a flat profile, it may be desirable for the sensor 12 to be flat at a patient-contacting side 260 such that the sensor 12 is substantially free of any edges that may press into the patient's tissue 102 (FIG. 5). FIG. 19 depicts a cross-sectional view of an embodiment of the sensor 12 in which the patient-contacting adhesive layer 158 is substantially flush with the island padding layer 150 to reduce or eliminate the presence of protruding edges that could potentially create discomfort for the patient 40. Thus, when used in conjunction with the stepped and/or rounded edges discussed above, the sensor 12 may be substantially free of potentially uncomfortable edges.

Figure 20:
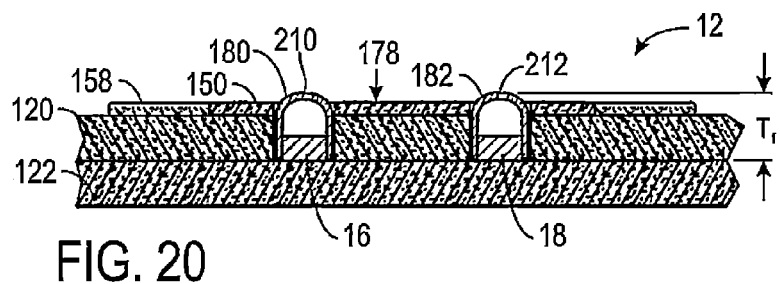
FIG. 20 is a cross-sectional view of an embodiment of the sensor of FIGS. 11 or 12 and illustrated as having compressible lenses that protrude beyond a padding layer of the sensor, in accordance with an aspect of the present disclosure.
Figure 21:
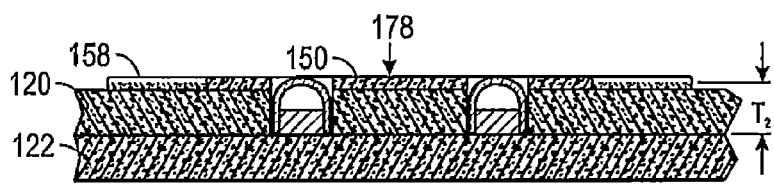
FIG. 21 is a cross-sectional view of an embodiment of the sensor of FIG. 21 and illustrated as having the lenses compressed, in accordance with an aspect of the present disclosure.

As noted above with respect to FIG. 11, the emitter and detector lenses 180, 182 may be formed from a compressible lens material, such as a material having a hardness on the Shore OO durometer scale of less than approximately 60, less than approximately 40, or less than approximately 20, such as a silicone gel. Indeed, the emitter and detector lenses 180, 182 may have respective Shore OO durometer values or Shore A durometer values that are greater than a Shore OO or a Shore A durometer value, respectively, of the island padding layer 150, and less than approximately 60 or less than approximately 40 on the Shore OO durometer scale. FIGS. 20 and 21 depict an embodiment of the sensor 12 in which the emitter and detector lenses 180, 182 are formed from such a material. In FIG. 20, the respective patient-facing surfaces 210, 212 of the emitter and detector lenses 180, 182 protrude beyond the patient-contacting surface 178 of the island padding layer 150, such that the emitter and detector lenses 180, 182 have a first thickness $T_1$.

As the sensor 12 of FIG. 20 is secured to and pressed against the patient 40, the emitter and detector lenses 180, 182 may compress to a second thickness $T_2$, as illustrated in FIG. 21. Accordingly, in one embodiment, the respective patient-facing surfaces 210, 212 of the emitter and detector lenses 180, 182 may move such that they become substantially flush with the patient-contacting surface 178 of the island padding layer 150, as illustrated. However, in other embodiments, the respective patient-facing surfaces 210, 212 of the emitter and detector lenses 180, 182 may move below or may remain above the patient-contacting surface 178. For example, in an embodiment where the emitter and detector lenses 180, 182 have a durometer value that is less than the island padding layer 150, the respective patient-facing surfaces 210, 212 of the emitter and detector lenses 180, 182 may move below the patient-contacting surface 178, depending on the degree to which the sensor 12 is pressed against the patient 40. Similarly, in an embodiment where the emitter and detector lenses 180, 182 have a durometer value that is greater than the island padding layer 150, the respective patient-facing surfaces 210, 212 of the emitter and detector lenses 180, 182 may remain above the patient-contacting surface 178.

Figure 23:
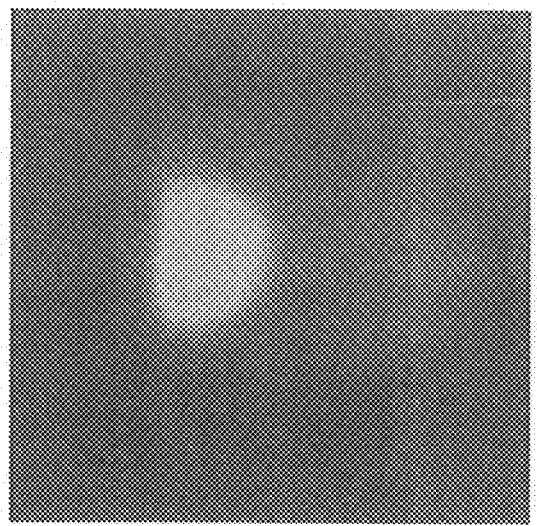
FIG. 23 is an illustration of an embodiment of the pressure profile created by an embodiment of the sensor of FIGS. 1, 3, 11, and 12, in accordance with an aspect of the present disclosure.
Figure 22:
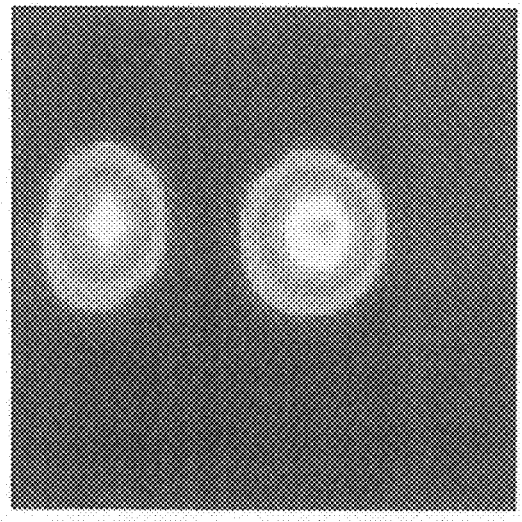
FIG. 22 is an illustration of an embodiment of a pressure profile created by an embodiment of the sensor of FIGS. 1 and 3, in accordance with an aspect of the present disclosure.

As noted above, any of the approaches described herein for reducing the pressure of the sensor 12 against the patient 40 may be used in any combination. Indeed, the present embodiments provide a variety of approaches for reducing shearing and strain forces on the patient's tissue that may be caused by edges and protrusions of the sensor 12. FIGS. 22 and 23 provide a comparison between a conventional sensor and a sensor configured in accordance with certain of the present embodiments. Specifically, FIGS. 22 and 23 depict pressure profiles produced on a forehead and skin model using a conventional sensor and an embodiment of the sensor 12 having compressible lenses and the island padding layer, respectively. A headband was used with both sensors at full (100%) tension. Further, the pressure profile data used to generate the images in FIGS. 22 and 23 is normalized.

The pressure profile of FIG. 22 depicts two distinct regions corresponding to an emitter and a detector of the conventional sensor, with the increased contrast in the image resulting from relatively high levels of pressure created by the protruding, relatively non-compressible (i.e., non-compressible at the forces generated using a headband) emitter and detector lenses of the conventional sensor. Conversely, the pressure profile of FIG. 23 depicts only one region corresponding to the position of the emitter 16 of the sensor 12. It may be appreciated that the decreased level of contrast in the image of FIG. 23 compared to that of the image in FIG. 22 is indicative that the sensor 12 configured in accordance with the present disclosure produces fewer areas of increased pressure, and a lower overall pressure level of the sensor 12 against the patient 40.

As noted above, in addition to, or in lieu of, ensuring a comfortable fit using the approaches described with respect to FIGS. 6-21, it may be desirable to increase the efficiency of light transmission through the emitter and detector lenses 180, 182 of the sensor 12. Indeed, increasing the efficiency of light transmission may enable the sensor 12 to be used at a lower pressure than would otherwise be suitable for obtaining accurate measurements. Such embodiments are discussed with respect to FIGS. 24-27.

Figure 24:
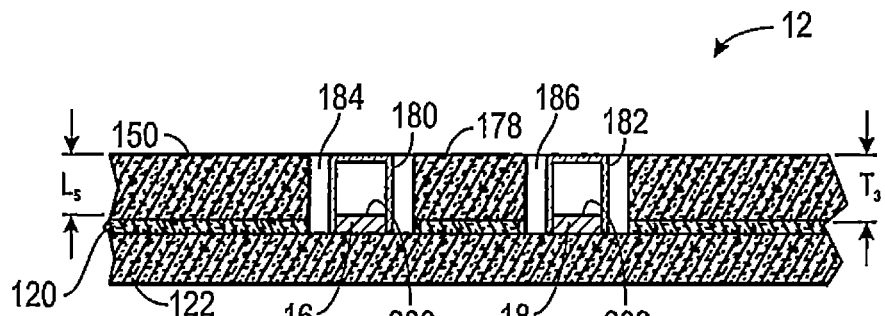
FIG. 24 is a cross-sectional view of an embodiment of the sensor of FIGS. 1, 3, 11, and 12, illustrating the emitter and the detector as being positioned closer to a patient-facing surface of the sensor, in accordance with an aspect of the present disclosure.

In FIG. 24, an embodiment of the sensor 12 is depicted in a cross-sectional view as having the emitter 16 and the detector 18 placed relatively close to the patient 40 compared to an original or typical configuration. For example, the features of the sensor 12 that affect a distance or length $L_5$ between an active face 280 of the emitter 16 or an active face 282 of the detector 18 and the patient 40 may be reduced compared to an original or typical configuration. It may be desirable to reduce the length $L_5$ to enhance the amount light transmitted to and received from the patient 40 by the emitter 16 and the detector 18, respectively. In the illustrated embodiment, reducing the distance between the active faces 280, 282 of the emitter 16 and detector 18 and the patient 40 may include reducing a thickness $T_3$ of the island padding layer 150, reducing a thickness of the emitter and detector lenses 180, 182, or a combination thereof.

The thickness $T_3$ of the island padding layer 150 may be selected so as to enable the emitter 16 and the detector 18 to be as close to the patient's tissue 102 (FIG. 5) as possible, while maintaining an acceptable amount of the pressure-relieving properties provided by the island padding layer 150 discussed above. Generally, any suitable thickness $T_3$ for the island padding layer 150 is presently contemplated. As a non-limiting example, the thickness $T_3$ of the island padding layer 150 may be approximately 0.045 inches (in).

A reduction in the thickness of the emitter and/or detector lenses 180, 182 compared to an original or typical configuration may include using different lens materials for the emitter and/or detector lenses 180, 182. In one embodiment, this may include using pre-fabricated lenses rather than lenses that are cured in place (i.e., cured within the second emitter and detector openings 184, 186 of the island padding layer 150). By way of a non-limiting example, this may include using silicone-based pre-fabricated lenses rather than lenses produced from a cured material, such as a cured PVC, a cured epoxy, or a similar curable material.

Figure 25:
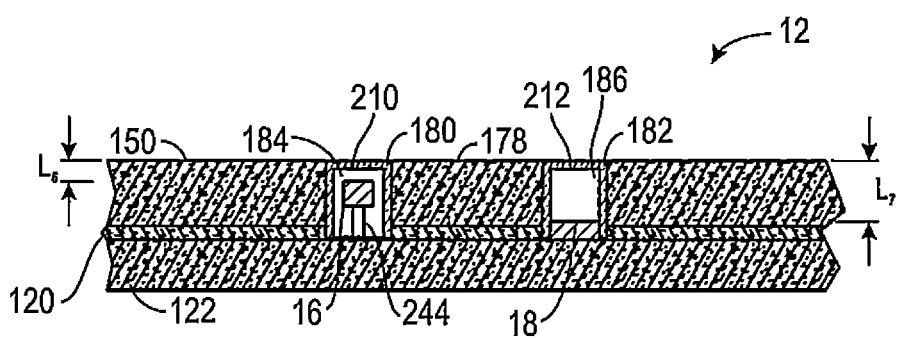
FIG. 25 is a cross-sectional view of an embodiment of the sensor FIGS. 1, 3, 11, and 12, and illustrating the emitter and the detector as having different distances from the patient, in accordance with an aspect of the present disclosure.

In addition to, or as an alternative to moving both the emitter 16 and the detector 18 closer to the patient 40, in certain embodiments the emitter 16 and the detector 18 may be provided at different lengths or distances $L_6$, $L_7$, respectively, from the respective patient-facing surfaces 210, 212 of the emitter and detector lenses 180, 182, as illustrated in the cross-sectional view of FIG. 25. For example, in the illustrated embodiment of the sensor 12 in FIG. 25, the emitter 16 is depicted as being closer to the patient-facing surface 210 of the emitter lens 180 than the detector 18 is to the patient-facing surface 212 of the detector lens 182. That is, $L_6$ may be smaller than $L_7$. To produce the offset configuration illustrated in FIG. 25, the emitter 16 may be a surface mount emitter that is floated within the second emitter opening 184 of the island padding layer 150. The emitter 16 may be floated by positioning the emitter 16 directly above the first set of conductors 244 such that the first set of conductors 244 temporarily support the emitter 16. A curable lens material (e.g., a curable silicone) used to produce the emitter lens 180 may then be disposed and cured within the second emitter opening 184 to hold the emitter 16 in place.

Figure 26:
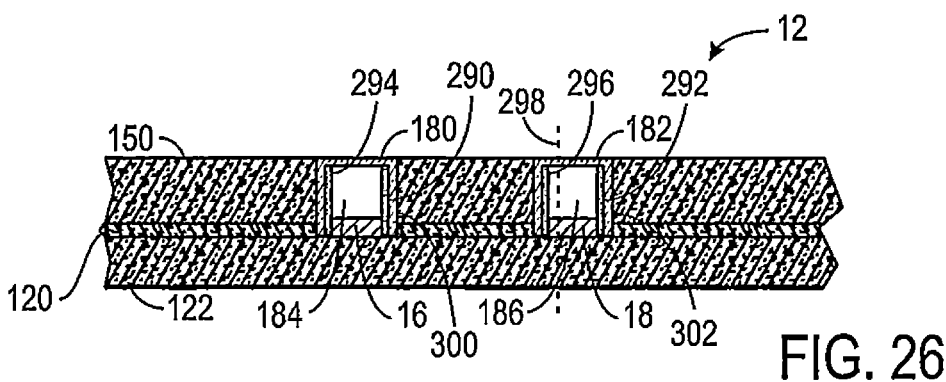
FIG. 26 is a cross-sectional view of an embodiment of the sensor of FIGS. 1, 3, 11, and 12, illustrating the lenses of the emitter and the detector as having a reflective material disposed within or on their respective inner walls, in accordance with an aspect of the present disclosure.

In addition to, or in lieu of adjusting the positioning of the emitter 16 and/or detector 18 as described above, one or more reflective and/or transmissive materials may be disposed on or included within an emitter lens inner wall 290 and/or a detector lens inner wall 292, as illustrated in the cross-sectional view of an embodiment of the sensor 12 in FIG. 26. In FIG. 26, the emitter and detector lenses 180, 182 are depicted as having respective coatings 294, 296 disposed on the emitter lens inner wall 290 and the detector lens inner wall 292. The coatings 294, 296 may be configured to increase the reflectance and/or transmission of the wavelengths of light used for measuring one or more physiological parameters of the patient 40 along respective light paths generally defined by the emitter lens inner wall 290 and the detector lens inner wall 292. For example, the coatings 294, 296 may be configured to increase the reflectance and/or transmission of IR, near IR, or similar wavelengths of light generally along an axial direction 298 of the emitter and detector lenses 180, 182.

In embodiments where the coatings 294, 296 are configured to increase light reflectance within the emitter and detector lenses 180, 182, the coatings 294, 296 may include or be formed from one or more reflective materials. The one or more reflective materials may include a metalized paint (e.g., a reflective metal ink), a foil, a metalized tape (e.g., an aluminum tape), a white paint such as an acrylic paint and/or a metal oxide-doped paint (e.g., a paint having titanium dioxide to increase the whiteness of the paint), or any combination thereof. Generally, the one or more reflective materials may increase the reflectance of the wavelengths of interest within the emitter and detector lenses 180, 182 such that in one embodiment, total internal reflection (TIR) may be obtained for the wavelengths of interest.

In certain embodiments, a reflective material may be mixed with the curable material used to produce the lenses 180, 182, in addition to or in lieu of being coated onto the lenses 180, 182. For example, respective inner walls 300, 302 of the second emitter and detector openings 184, 186 may be coated with a mixture including the pre-cured lens material that is used to produce the emitter and detector lenses 180, 182 and one or more reflective materials. Therefore, in such embodiments, the emitter and detector lenses 180, 182 may include, at an area of the lenses 180, 182 corresponding to the inner walls 300, 302 (e.g., emitter lens inner wall 290 and the detector lens inner wall 292), the one or more reflective materials. In one non-limiting example, a curable mixture, such as a curable silicone mixture, may be mixed with a reflective material, such as titanium dioxide, to produce increased levels of white in the curable mixture. Accordingly, upon curing, the emitter and detector lenses 180, 182 may have an inherently white color (i.e., a reflective color) along their respective areas corresponding to the inner walls 300, 302 of the second emitter and detector openings 184, 186.

In further embodiments, it may be desirable to, additionally or alternatively, provide one or more materials that are capable of configuring the emitter lens inner wall 290 and the detector lens inner wall 292 to act as multi-modal optical fibers. Thus, the inner walls 300, 302 of the second emitter and detector openings 184, 186 may act as a cladding for the lenses 180, 182. In this example, the area of the emitter and detector lenses 180, 182 corresponding to the inner walls 300, 302 of the second emitter and detector openings 184, 186 (e.g., the emitter lens inner wall 290 and the detector lens inner wall 292) may be coated with or include any one or a combination of optical fiber materials such as silica, fluorided silica, phosphate glass materials, chalcogenide materials, or any such optical fiber material. Again, in one embodiment, the emitter lens inner wall 290 and the detector lens inner wall 292 may be configured to provide TIR for the wavelengths of interest for monitoring the patient's physiological parameters.

Figure 27:
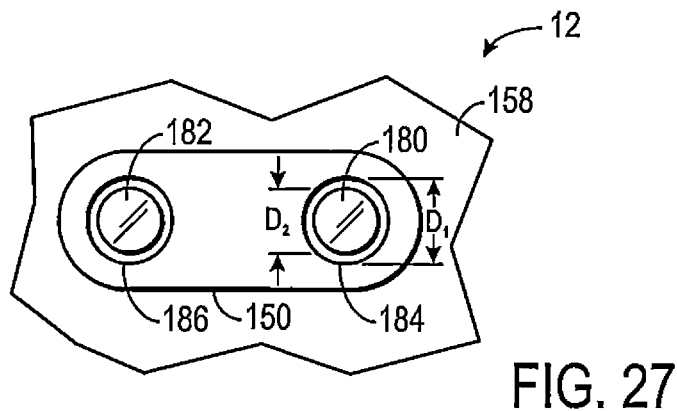
FIGS. 27 is a top view of an embodiment of the sensor of FIGS. 1, 3, 11, and 12, and illustrating an outermost padding layer as having oversized openings for the emitter and detector lenses, in accordance with an aspect of the present disclosure.

While the emitter and detector lenses 180, 182 may be disposed within the second emitter and detector openings 184, 186 of the island padding layer 150, it should be noted that they may, in some embodiments, not be in direct abutment with the respective inner surfaces 300, 302 of the second emitter and detector openings 184, 186. For example, in embodiments where the emitter and detector lenses 180, 182 are pre-fabricated lenses, it may be difficult to properly position them within the second emitter and detector openings 184, 186 of the island padding layer 150 if the emitter and detector lenses 180, 182 are configured to be in direct abutment with the respective inner surfaces 300, 302. Thus, it may be desirable to have second emitter and detector openings 184, 186 with larger circumferences than the emitter and detector lenses 180, 182. Such an embodiment is illustrated in FIG. 27, which is a top-down view of a portion of the sensor 12 taken within line 27-27 of FIG. 13.

By way of example, such a configuration may be desirable to facilitate the use of pre-fabricated emitter and detector lenses 180, 182, which may be positioned within the emitter and detector openings 184, 186 after the layers of the sensor 12 (e.g., the first, second, and island padding layers 120, 122, 150) have been assembled. Pre-fabricated lenses, in certain embodiments, may provide enhanced light transfer compared to lenses that are formed by curing within the openings 184, 186. Further, using pre-fabricated lenses also enables the integration of reflective materials on and/or within the emitter and detector lenses 180, 182, as described above with respect to FIG. 26.

Thus, the openings 184, 186 may have circumferences that are larger than the respective circumferences of the emitter and detector lenses 180, 182, respectively. For example the openings 184, 186 may have circumferences that are at least approximately 1% larger, such as between approximately 5% and 50% larger, than the circumferences of the emitter and detector lenses 180, 182. Therefore, the openings 184, 186 may have respective diameters $D_1$ that are that are at least approximately 5% larger, such as between approximately 5% and 50% larger, than respective diameters $D_2$ of the emitter and detector lenses 180, 182.

Figure 28:
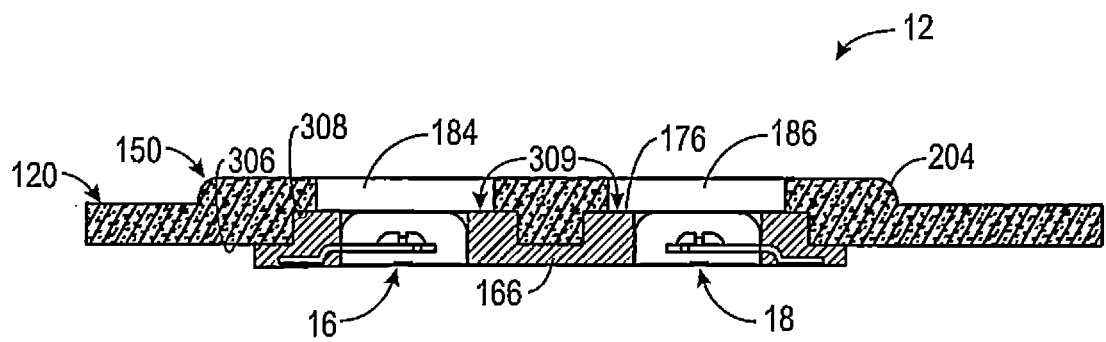
FIG. 28 is a cross-sectional view of an embodiment of the sensor of FIG. 13 taken within line 28-28 and illustrating one example of the respective positioning of the emitter, detector, the semi-rigid optical mount, and the one-piece island and first padding layer of FIG. 12, in accordance with an aspect of the present disclosure.

As noted above, the emitter and detector lenses 180, 182 are respectively positioned within the openings 184, 186 and on the surface 176 of the semi-rigid optical mount 166. An embodiment of the respective positioning of the single molded piece 204, the optical mount 166, the emitter 16, the detector 18, and the openings 184, 186 is illustrated in FIG. 28. Specifically, FIG. 28 is a cross-sectional side view taken within line 28-28 of FIG. 13. In FIG. 28, the single molded piece 204 is positioned directly over the semi-rigid optical mount 166. A first inner surface 306 corresponding to the first padding layer 120 portion of the single molded piece 204 partially abuts the optical mount 166, while a second inner surface 308 corresponding to the island padding layer 150 portion of the single molded piece 204 fully abuts (i.e., is in complete contact with) the optical mount 166. A portion 309 of the surface 176 of the semi-rigid optical mount 166 is not in contact with any of the padding layers, and is configured to abut the emitter lens 180 (FIG. 12) in the emitter opening 184 and the detector lens 182 (FIG. 12) in the detector opening 186.

As discussed with respect to FIG. 11, in certain embodiments, it may be desirable to retain the emitter and detector lenses 180, 182 within their respective openings 184, 186 using features such as tapes (e.g., polygonal and/or rounded tapes), adhesives, and the like. In other embodiments, however, it may be desirable to reduce the part count of the sensor 12 and/or reduce the number of overall steps suitable for assembling the sensor 12 to facilitate its manufacture. Accordingly, it may be desirable to retain the emitter and detector lenses 180, 182 without the use of circular tapes or adhesives. One embodiment of such an approach is illustrated in FIG. 29.

Figure 29:
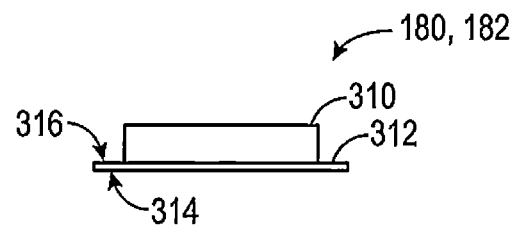
FIG. 29 is a side view of an embodiment of a lens adapted to be fitted over the emitter or the detector of the sensor of FIGS. 1, 3, 11, and 12, the lens having a flange configured to facilitate retention of the lens within the sensor, in accordance with an aspect of the present disclosure.

Keeping in mind the configuration described above with respect to FIG. 28, in FIG. 29, the emitter/detector lens 180, 182 includes a main portion 310 and a flange portion 312. The main portion 310 serves as a portion of the light path from/to the emitter 16 and detector 18, and the flange portion 312 is configured to abut both the surface 176 of the semi-rigid optical mount 166 and the second inner surface 308 of the single molded piece 204. Specifically, a first surface 314 of the flange portion 312 may abut the surface 176 of the optical mount 166, while a second surface 316 abuts the second inner surface 308 of the single molded piece. In such a configuration, the flange portion 312 enables retention forces to form between the emitter/detector lens 180, 182, the optical mount 166, and the single molded piece 204 when the sensor 12 is assembled. In other words, the flange portion 312 is configured to facilitate retention of the emitter/detector lens 180, 182 within the sensor 12. For example, the retention forces enabled by the presence of the flange portion 312 may be sufficient to overcome adhesive forces created between the material of the emitter/detector lens 180, 182 (e.g., silicone) and the patient's tissue 102 (FIG. 5). Other configurations of the emitter and the detector lenses 180, 182 in which one or more flanges retain the lenses 180, 182 within the sensor 12 are also presently contemplated. For example, keeping in mind the configuration of FIGS. 28 and 29, the emitter and detector lenses 180, 182 may include the flange portion 312 that is positioned between the second inner surface 308 and the optical mount 166 as well as an additional flange that is positioned between first inner surface 306 and the optical mount 166. Accordingly, the lens 180, 182 may include one or more flanges to enable its retention within the sensor 12. Alternatively, embodiments in which the lens 180, 182 is sized such that the flange portion 312 is configured to be positioned between the first inner surface 306 and the optical mount 166 are also contemplated. In such configurations, the single molded piece may only include the first inner surface 306 and not the second inner surface 308.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A spectrophotometric medical sensor, comprising:
   a first padding layer;
   a second padding layer secured to the first padding layer and comprising an emitter well and a detector well;
   an emitter positioned within the emitter well and configured to transmit one or more wavelengths of light toward a patient's tissue;
   a detector positioned within the detector well and configured to receive the one or more wavelengths of light transmitted by the emitter to measure a physiological parameter of the patient; and
   an island padding layer secured to a patient-facing side of the second padding layer such that the island padding layer is the closest padding layer to the patient's tissue when the sensor is placed on the patient to measure the physiological parameter, the island padding layer comprising an emitter opening and a detector opening, wherein the emitter and detector openings are distinct from one another and are configured to enable light transmission from and to the emitter and the detector, respectively, and the second padding layer defines a periphery that is larger than the island padding layer.

2. The medical sensor of claim 1, wherein the island padding layer and the second padding layer are molded as a single piece.

3. The medical sensor of claim 1, wherein the island padding layer and the second padding layer are adhesively secured to one another.

4. The medical sensor of claim 1, wherein the first, second, and island padding layers are opaque with respect to the one or more wavelengths of light transmitted by the emitter and detected by the detector.

5. The medical sensor of claim 1, wherein the first padding layer, the second padding layer, the island padding layer, or any combination thereof, comprise rounded edges.

6. The medical sensor of claim 1, wherein the periphery defined by the second padding layer is larger than the first padding layer.

7. The medical sensor of claim 1, comprising an emitter lens and a detector lens disposed over the emitter and detector, respectively, wherein the emitter lens and the detector lens comprise respective patient-facing surfaces that are substantially flush with a patient-facing surface of the island padding layer.

8. The medical sensor of claim 1, comprising an emitter lens and a detector lens disposed over the emitter and detector, respectively, wherein the emitter lens and the detector lens comprise respective inner walls and one or more reflective materials disposed on the respective inner walls, wherein the one or more reflective materials are configured to increase light transmission through the emitter lens and the detector lens.

9. The medical sensor of claim 8, wherein the one or more reflective materials comprise a metalized paint, a foil, a metalized tape, a white paint, or a combination thereof, and the emitter lens and the detector lens comprise pre-formed lenses.

10. The medical sensor of claim 1, comprising a compressible emitter lens and a compressible detector lens disposed over the emitter and detector, respectively, wherein the compressible emitter lens and the compressible detector lens have respective Shore OO durometer values that are greater than a Shore OO durometer value of the island padding layer and less than approximately 60 on the Shore OO durometer scale.

11. The medical sensor of claim 10, wherein the compressible emitter lens and the compressible detector lens comprise respective patient-facing surfaces that are substantially flush with or protrude beyond a patient-facing surface of the island padding layer.

12. The medical sensor of claim 1, comprising an emitter lens and a detector lens disposed over the emitter and detector, respectively, wherein the respective circumferences of the second emitter opening and the second detector of the island padding layer are at least approximately 5% larger than the respective circumferences of the emitter lens and the detector lens.

13. The medical sensor of claim 1, comprising an emitter lens and a detector lens disposed over the emitter and detector, respectively, wherein the emitter lens and the detector lens comprise respective patient-facing surfaces that are closer to the first padding layer than a patient-facing surface of the island padding layer, and the respective patient-facing surfaces of the emitter lens and the detector lens are configured to be substantially flush with or protrude beyond the patient-facing surface of the island padding layer when the medical sensor is compressed against the patient.

14. The medical sensor of claim 1, comprising an adhesive layer secured to the second padding layer and about the island padding layer and configured to secure the medical sensor to the patient, wherein the adhesive layer comprises a patient-contacting surface that is substantially flush with a patient-contacting surface of the island padding layer such that a patient-contacting side of the medical sensor has a substantially flat profile.

15. The medical sensor of claim 1, comprising a plurality of stacked adhesive layers secured to the second padding layer, each stacked layer of the plurality of stacked adhesive layers being configured to secure the medical sensor to the patient and comprising an opening enabling the respective adhesive layer to be positioned about the island padding layer.

16. A medical sensor, comprising:
   a first padding layer;
   a second padding layer secured to the first padding layer and comprising an emitter opening and a detector opening, wherein the second padding layer defines a periphery that is greater than the first padding layer in an area of the sensor that contacts a patient's tissue;
   an emitter positioned within the emitter opening and configured to transmit one or more wavelengths of light toward the patient's tissue; and
   a detector positioned within the detector opening and configured to receive the one or more wavelengths of light transmitted by the emitter to measure a physiological parameter of the patient; and wherein the second padding layer is positioned between a patient-contacting surface of the medical sensor and the first padding layer, and an outer edge of the periphery of the second padding layer is configured to curve in a direction generally away from the patient as the medical sensor is compressed against the patient's tissue.

17. The medical sensor of claim 16, comprising an island padding layer secured to a patient-facing side of the second padding layer, the island padding layer comprising first and second openings corresponding to the emitter and the detector, respectively, wherein the first and second openings are distinct and the island padding layer has a periphery that is smaller than the the second padding layer.

18. The medical sensor of claim 16, wherein the emitter and the detector are positioned in a generally central portion of the medical sensor, and a profile of the medical sensor is tapered such that the medical sensor comprises a thickness that is greater in the central portion and is reduced toward an outer edge of the medical sensor.

19. The medical sensor of claim 18, wherein the first and second padding layers each have a respective thickness that is greater in the central portion than at their respective outer edges.

20. The medical sensor of claim 16, wherein the first padding layer comprises an outward-facing surface having a substantially flat profile, and the substantially flat profile is configured to enable the medical sensor to place a substantially even pressure on the patient's tissue as the medical sensor is pressed against the patient.

21. A patient monitoring system, comprising:
a medical sensor, comprising:
a first padding layer;
a second padding layer secured to the first padding layer and comprising an emitter well and a detector well;
an emitter positioned within the emitter well and configured to transmit one or more wavelengths of light toward a patient's tissue;
an emitter lens disposed over the emitter and comprising an emitter lens surface adapted to face the patient's tissue upon placement of the medical sensor on the patient;
a detector positioned within the detector well and configured to receive the one or more wavelengths of light transmitted by the emitter to measure a physiological parameter of the patient;
a detector lens disposed over the detector and comprising a detector lens surface adapted to face the patient's tissue upon placement of the medical sensor on the patient; and
an island padding layer secured to the second padding layer and comprising a second emitter opening and a second detector opening, wherein the second emitter and detector openings are distinct from one another and are configured to enable light transmission from and to the emitter and the detector, respectively, and wherein the island padding layer defines a periphery that is smaller than the second padding layer.

22. The patient monitoring system of claim 21, wherein the emitter lens surface and the detector lens surface are substantially flush with one another, a first distance from the emitter to the emitter lens surface is less than a second distance from the detector to the detector lens surface, and the emitter lens and the detector lens are formed around the emitter and the detector, respectively.

23. The patient monitoring system of claim 21, comprising a sensor cable having a first set of conductors and a second set of conductors coupled to the emitter and the detector, respectively, and the sensor cable comprises a flat portion configured to be placed against the patient's tissue.

24. The patient monitoring system of claim 23, wherein the sensor cable is rounded on a side positioned opposite the flat portion.

25. The patient monitoring system of claim 23, wherein the sensor cable comprises a ribbon cable or a flexible circuit cable comprising a polymeric dielectric material, wherein the first and second sets of conductors are disposed on the polymeric dielectric material.

26. The patient monitoring system of claim 23, wherein the first padding layer comprises an outer surface and the second padding layer comprises a patient-facing surface, and a thickness defined by a distance between the outer surface and the patient-facing surface is greater than a circumference of the sensor cable.

27. The patient monitoring system of claim 23, comprising a physiological monitor adapted to receive a connector of the sensor cable, wherein the sensor cable is adapted to provide an interface between the physiological monitor and the medical sensor.

28. The patient monitoring system of claim 27, wherein the physiological monitor comprises a pulse oximetry monitor and the medical sensor comprises a pulse oximetry sensor.

29. The patient monitoring system of claim 21, comprising a headband associated with the medical sensor, wherein the headband is configured to apply a normal force within a desired range against the medical sensor to enable the medical sensor to accurately measure the physiological parameter of the patient.

30. The patient monitoring system of claim 29, wherein the emitter lens surface and the detector lens surface are recessed within the island padding layer and are configured to be substantially flush with or protrude beyond the island padding layer and into the patient tissue upon application of the normal force within the desired range using the headband.

* * * * *